United States Patent [19]

Singer et al.

[11] Patent Number: 5,573,909
[45] Date of Patent: Nov. 12, 1996

[54] FLUORESCENT LABELING USING MICROPARTICLES WITH CONTROLLABLE STOKES SHIFT

[75] Inventors: Victoria L. Singer; Richard P. Haugland, both of Eugene, Oreg.

[73] Assignee: Molecular Probes, Inc., Eugene, Oreg.

[21] Appl. No.: 247,108

[22] Filed: May 20, 1994

Related U.S. Application Data

[63] Continuation-in-part of Ser. No. 882,299, May 13, 1992, Pat. No. 5,362,692.

[51] Int. Cl.$^6$ .......................... C12Q 1/68; G01N 33/545
[52] U.S. Cl. .................... 435/6; 435/5; 435/7.1; 436/518; 436/528; 436/531; 436/532; 436/533; 436/534; 436/546; 436/172; 436/805
[58] Field of Search ............... 435/6, 5, 7.1, 7.2, 435/7.21, 7.24, 7.32; 436/501, 518, 528, 529, 530, 531, 532, 533, 534, 546, 172, 800, 805

[56] References Cited

U.S. PATENT DOCUMENTS

| | | | |
|---|---|---|---|
| 2,994,697 | 8/1961 | Eckert et al. | 548/110 |
| 3,096,333 | 7/1963 | Wilson et al. | 548/110 |
| 4,326,008 | 4/1982 | Rembaum | 428/403 |
| 4,520,110 | 5/1985 | Stryer et al. | 436/501 |
| 4,542,104 | 9/1985 | Stryer et al. | 436/536 |
| 4,666,862 | 5/1987 | Chan | 436/501 |
| 4,707,454 | 11/1987 | Hendrix | 436/546 |
| 4,774,339 | 9/1988 | Haugland et al. | 548/405 |
| 4,808,524 | 2/1989 | Snyder et al. | 435/36 |
| 4,916,711 | 4/1990 | Boyer et al. | 372/53 |
| 4,996,143 | 2/1991 | Heller et al. | 435/6 |
| 4,997,597 | 3/1991 | Clough et al. | 252/646 |
| 5,187,288 | 2/1993 | Kang et al. | 548/110 |
| 5,248,782 | 9/1993 | Haugland et al. | 548/110 |
| 5,326,692 | 7/1994 | Brinkley et al. | 435/6 |

FOREIGN PATENT DOCUMENTS 1434743 of 1976 United Kingdom.

OTHER PUBLICATIONS

Molday et al., J. Cell Biol. 64, 75 (1975).
Margel et al., J. Cell Sci. 56, 157 (1982).
Haugland, *Fluorescein Substitutes for Microscopy and Imaging*, Optical Microscopy for Biology pp. 143–157 (1990).
Oi et al., J. Cell Bio. 93, 981 (1982).
Gorelenko et al., *Photonics of Bichromophores Based on Laser Dyes in Solutions and Polymers*, Experimentelle Technik Der Physik 37, 343 (1989).
Jullien et al., Biochem., 22, 3829 (1983).
Wooley et al., Biophys. Chem. 26, 367 (1987).
Ohmine et al., Macromolecules 10, 862 (1977).
Drake et al., Science 251, 1574 (1991).
Saito et al., Appl. Chem. 11, 345 (1966).
Kuhn, Chem. Abstracts 66, 671 (1967).
Yamazaki et al., J. Phys. Chem. 94, 516 (1990).
Mataga et al., J. Phys. Chem. 73, 370 (1969).
Bennett, J. Chem. Physics 41, 3037 (1964).
Bangs (Uniform Latex Particles (1984, Seragen, Inc.).
Guilford, Chem. Soc. Rev. 2, 249 (1973).
Nathan, et al., J. Exp. Med. 154, 1539 (1981).
Kremsky et al., Nucleic Acids Res. 15, 2891 (1987).
Cytometry 11, 126 (1990).
Haughland, Molecular Probes Handbook of Fluorescent Probes and Research Chemicals (1992–1994).
Rapoport et al., J. Am. Chem. Soc. 84, 2178 (1962).
Silverstein et al., Org. Synth. 4, 831.
Larison et al., Development 109, 567 (1990).
Vener et al., Anal. Biochem. 198, 308 (1991).
Jett et al., Flow Cytometry & Sorting, 2, 381 (1990).
Hook et al., J. Leukocyte Biol. 45, 277 (1989).
Wolf et al., Nucleic Acids 15, 2911 (1987).
Cooper et al., Circulatory Shock 37, 5 (1992).
Fornusek et al., CRC Critical Reviews in Therapeutic Drug Carrier Systems 2, 137 (1986).
Molecular Probes product literature entitled "Novel Fluorescent Latex Microspheres".

*Primary Examiner*—Christina Y. Chan
*Assistant Examiner*—Lora M. Green
*Attorney, Agent, or Firm*—Allegra J. Helfenstein; Anton E. Skaugset

[57] ABSTRACT

The invention relates to methods for labeling or detecting one or more target materials using surface coated fluorescent microparticles with unique characteristics. The unique microparticles used to practice the invention have at least two components: an external substance or coating that is selective for each target material and an internal mixture of multiple fluorescent dyes. The mixture of dyes is a series of two or more fluorescent dyes having overlapping excitation and emission spectra allowing efficient energy transfer from the excitation wavelength of the first dye in the series, transfer through the dyes in the series and re-emitted as an optical signal at the emission wavelength of last dye in the series, resulting in a desired effective Stokes shift for the microparticle that is controlled through selection of appropriate dyes. The unique microparticles are combined with a sample thought to contain the target material(s), so that the microparticles label the target materials. The sample is then optionally illuminated, resulting in fluorescence of the microparticles that is used to detect one or more target materials.

30 Claims, 6 Drawing Sheets

Figure 2
Figure 2A
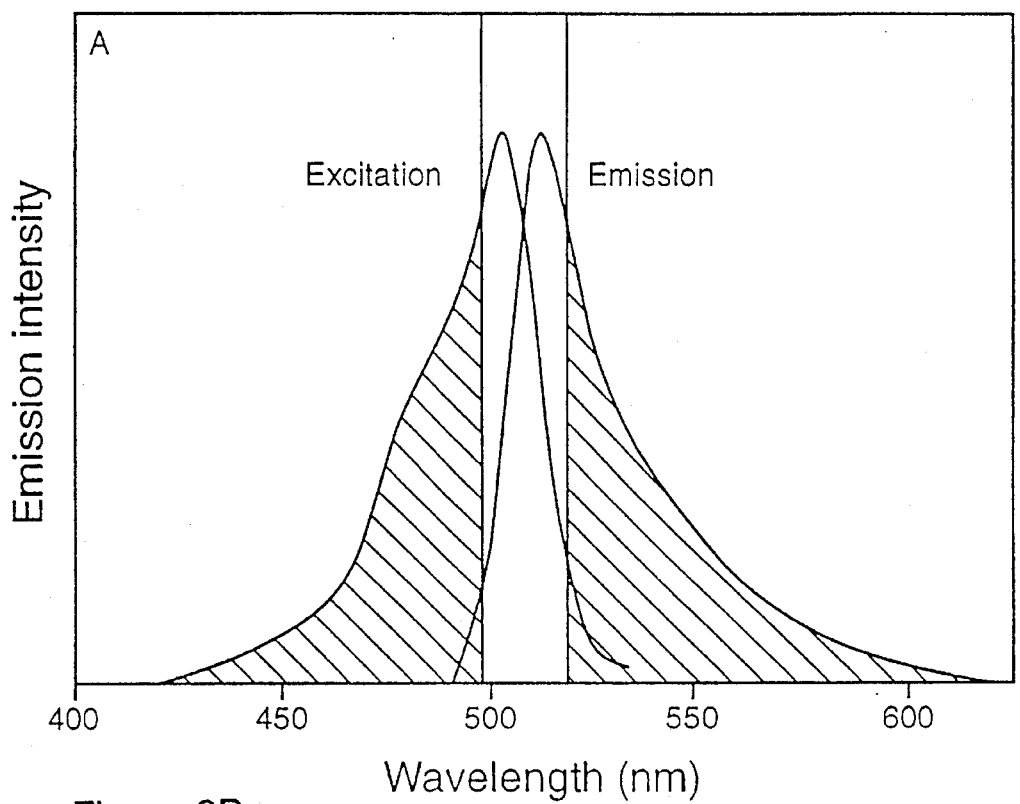
Figure 2B
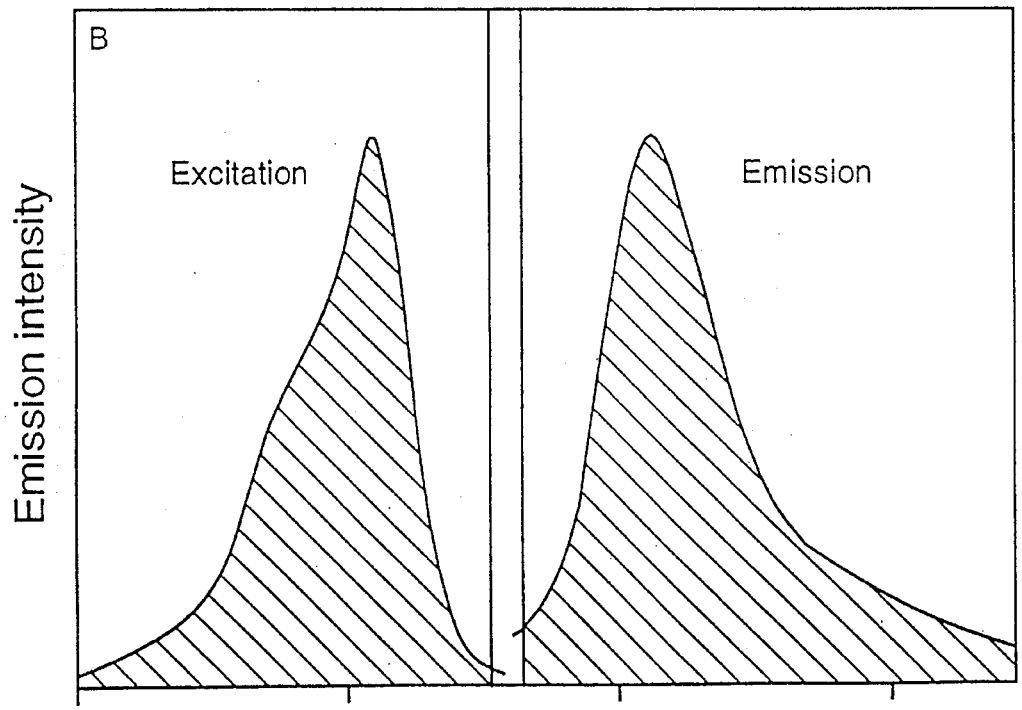

FLUORESCENT LABELING USING MICROPARTICLES WITH CONTROLLABLE STOKES SHIFT

This application is a continuation-in-part of application Ser. No. 07/882,299 filed May 13, 1992 now U.S. Pat. No. 5,362,692.

FIELD OF THE INVENTION

The invention relates to methods of labeling target materials using fluorescent microparticles having a surface coating that is selective for the target materials. The coated microparticles incorporate a series of two or more fluorescent compounds having overlapping excitation and emission spectra, resulting in fluorescent microparticles with a desired effective Stokes shift. The coated microparticles are useful for the detection of a wide variety of materials, including biological and synthetic molecules.

BACKGROUND OF THE INVENTION

Microparticles labeled with fluorescent dyes have found use in a wide variety of applications. Fluorescent microparticles are most commonly used in applications that can benefit from use of monodisperse, chemically inert particles that emit detectable fluorescence and that can bind to a particular substance in the environment. The high surface area of microparticles provides an excellent matrix for attaching molecules that selectively bind to targets, while the fluorescent properties of these particles enable them to be detected with high sensitivity. They can be quantitated by their fluorescence either in aqueous suspension or when captured on membranes.

Many luminescent compounds are known to be suitable for imparting bright and visually attractive colors to various cast or molded plastics such as polystyrene and polymethyl methacrylate. Uniform fluorescent latex microspheres have been described in patents (U.S. Pat. No. 2,994,697, 1961; U.S. Pat. No. 3,096,333, 1963; Brit. Patent 1,434,743, 1976) and in research literature (Molday, et al., J. CELL BIOL. 64, 75 (1975); Margel, et al., J. CELL SCI. 56, 157 (1982)). A related patent application of one of the inventors (Brinkley, et al., Ser. No. 07/629,466, filed Dec. 18, 1990) describes derivatives of the dipyrrometheneboron difluoride family of compounds (derivatives of 4,4-difluoro-4-bora-3a,4a-diaza-s-indacene) as useful dyes for preparing fluorescent microparticles. This family of dyes possesses advantageous spectral data and other properties that result in superior fluorescent microparticles.

Although dipyrrometheneboron difluoride labeled materials are highly fluorescent and photochemically stable, a disadvantage of these fluorescent materials is their relatively small Stokes shift (the difference between the peak excitation and peak emission wavelengths) when only one dye is used. Because the optimum wavelength of the exciting light is close to the peak emission light, fluorescent particles with small Stokes shifts require precise excitation and emission filters to eliminate or reduce interference. The customary use of excitation filters blocks part of the excitation and emission light that would otherwise increase the efficiency of the fluorescence and reduces the intensity of the fluorescent signal. Fluorescent materials that incorporate bright fluorescent dyes with increased Stokes shifts permits maximum utilization of the available excitation and emission light, resulting in a greater fluorescent signal (see e.g. FIGS. 2A and 2B).

Another advantage of fluorescent materials with large Stokes shifts is that they can be more easily detected in the presence of other fluorescent materials. Immunoassays are typically carried out in body fluids which contain many endogenous fluorescent molecules, such as bilins, flavins and drugs. Since the vast majority of interfering fluorescent materials have relatively short Stokes shifts, the use of a fluorescent label that emits at a wavelength far greater than its excitation wavelength makes the label easier to distinguish from background fluorescence, since its fluorescent signal is emitted at a wavelength at which most background fluorescence is minimal.

A third advantage of fluorescent materials with large Stokes shift is their usefulness in detecting multiple analytes in a single sample using a single excitation wavelength. Using two or more different fluorescent labels, each of which can be excited at a particular wavelength (e.g. the 488 nm argon laser principal emission), the emission peaks of the different labels are detected at different wavelengths, where each emission spectrum is characteristic of a single analyte. In order to successfully accomplish this, the emission peaks of the fluorescent labels must be well-separated from each other so the correction factors between the various dyes are minimized. High photostability of the label is also beneficial. Fluorescent materials with a large Stokes shift can be used in combination with fluorescent materials with a smaller Stokes shift where both materials excite at the same wavelength, but emit at different wavelengths, giving multiple signals that can be resolved using optical filters or monochromators.

Unfortunately, fluorescent compounds useful as labeling reagents that have Stokes shifts of 50–100 nm as well as high fluorescence efficiency and emission wavelengths of greater than 500 nm required for detectability are relatively rare. (Haugland, *Fluorescein Substitutes for Microscopy and Imaging,* OPTICAL MICROSCOPY FOR BIOLOGY pp. 143–57 (1990). The magnitude of the Stokes shift in fluorescent dyes has been found to be generally inversely proportional to the high absorbance needed to ensure a strong signal. Fluorescent dyes in use as labeling reagents for biological molecules, such as xanthenes, dipyrrometheneboron difluorides, rhodamines and carbocyanines commonly have Stokes shifts of less than about 30 nm.

The lack of suitable fluorescent dyes with large Stokes shifts has led to the development and use of protein-based fluorophores known as phycobiliproteins as labels (e.g. U.S. Pat. Nos. 4,520, 110 and 4,542,104 both to Stryer, et al. (1985)). Like other fluorophores, they have been covalently attached to beads and macromolecules. See, e.g., Oi, et al., J. CELL BIO. 93, 981 (1982). These large bilin-containing molecules have the disadvantage of poor chemical stability, instability to photobleaching, limited long wavelength emission capability, bulky molecular size (MW>100,000 Daltons) and relatively high cost. Furthermore, only a few proteins of this type are known and one cannot select or appreciably adjust their spectral properties. In an effort to improve the fluorescent emission efficiency of phycobiliproteins without significantly increasing their molecular size, phycobiliproteins have been covalently coupled to the fluorescent dye Azure A (U.S. Pat. No. 4,666,862 to Chan (1987)).

It is known that covalent coupling of a pair of fluorophores results in a fluorescent dye with a larger Stokes shift than either of the individual dyes (e.g. Gorelenko, et al., *Photonics of Bichromophores Based on Laser Dyes in Solutions and Polymers,* EXPERIMENTELLE TECHNIK DER PHYSIK 37, 343 (1989)). As with the phycobiliproteins, this approach, although reportedly effective in increasing the Stokes shift, requires complex synthetic procedures to chemically couple the two dyes together and are limited by the number and location of available reactive sites. Furthermore, covalently linked molecules typically have sufficient freedom of movement that significant collisional deactivation occurs, leading to loss of energy by vibrational relaxation rather than by fluorescence. There is a need for a way of combining the spectral properties of dyes by methods other than complex covalent coupling to provide useful fluorescent labels with an enhanced effective Stokes shift.

Energy transfer has been demonstrated between dyes that have been coupled to macromolecules to study intramolecular distances and conformation in biomolecules, e.g., Jullien & Garel, BIOCHEM. 22, 3829 (1983); Wooley, et al., BIOPHYS. CHEM. 26, 367 (1987); and in polymer chains and networks, e.g. Ohmine, et al., MACROMOLECULES 10, 862 (1977); Drake, et al., SCIENCE 251, 1574 (1991). Energy transfer with resultant wavelength shifting has also been described for mixtures of dyes in lasing solutions, e.g. Saito, et al., APPL. PHYS. LETT. 56, 811 (1990). Energy transfer has been demonstrated between monomolecular layers of dyes and other organized molecular assemblies, e.g. Kuhn, *Production of Simple Organized Systems of Molecules*, PURE APPL. CHEM. 11, 345 (1966), abstracted in CHEM. ABSTRACTS 66, 671 (1967); Yamazaki, et al., J. PHYS. CHEM. 94, 516 (1990). Energy transfer between paired donor and acceptor dyes has also been demonstrated in polymer films as a way of studying the energy transfer dynamics, e.g. Mataga, et al., J. PHYS. CHEM. 73, 370 (1969); Bennett, J. CHEM. PHYSICS 41, 3037 (1964). Although the conformity of research results to Förster's theoretical formulation have been widely reported, utilitarian applications of the theory have been limited. The cited references neither anticipate nor suggest fluorescent microparticles incorporating a series of dyes to be used as labeling reagents with an enhanced effective Stokes shift.

The fluorescent microparticles used for the present invention are described generically and specifically in the parent application Ser. No. 07/882,299 (incorporated by reference) published as PCT International Publication No. WO 93/23492 on Nov. 25, 1993. Additional microparticles are described specifically in U.S. Pat. No. 5,433,896 to Kang et al. (1995) titled DIBENZOPYRROMETHENEBORON DIFLUORIDE DYES (incorporated by reference). Specifically in the co-pending application DIBENZOPYRROMETHENEBORON DIFLUORIDE DYES (incorporated by reference), filed of even date herewith by inventors Kang and Haugland. These microparticles, when used with a surface material that is selective for target molecules, provide labels having excitation and emission characteristics that are considered to be the most useful for the detection of specified target molecules or combinations of target molecules.

DESCRIPTION OF THE DRAWINGS

FIGS. 2A and 2B show in graphic form the increase in fluorescent signal that is attainable by increasing the Stokes shift from about 10 nm to 70 nm in 0.093 micrometer latex microparticles. The microparticles in Spectrum A (FIG. 2A) contain 16 µMol/g-latex of Compound 1, while the microparticles in Spectrum B (FIG. 2B) contain 16 µMol/g-latex of Compound 1 (donor) and 9.6 µMol/g-latex of Compound 3 (acceptor). The relative shaded areas show the optimum filter bandwidths that can be used in each of these microparticle preparations, demonstrating the increased signal that is obtainable from the microparticles containing the donor-acceptor dye pair.

Spectrum A results from particles containing a mixture of Compound 1 and Compound 3 (488/557);

Spectrum B results from particles containing the mixture of Spectrum A plus Compound 4 (488/605);

Spectrum C results from particles containing the mixture of Spectrum B plus Compound 6 (488/645);

Spectrum D results from particles containing the mixture of Spectrum C plus Compound 5 (488/679);

Spectrum E results from particles containing the mixture of Spectrum D plus Compound 7 (488/720).

Figure 4:
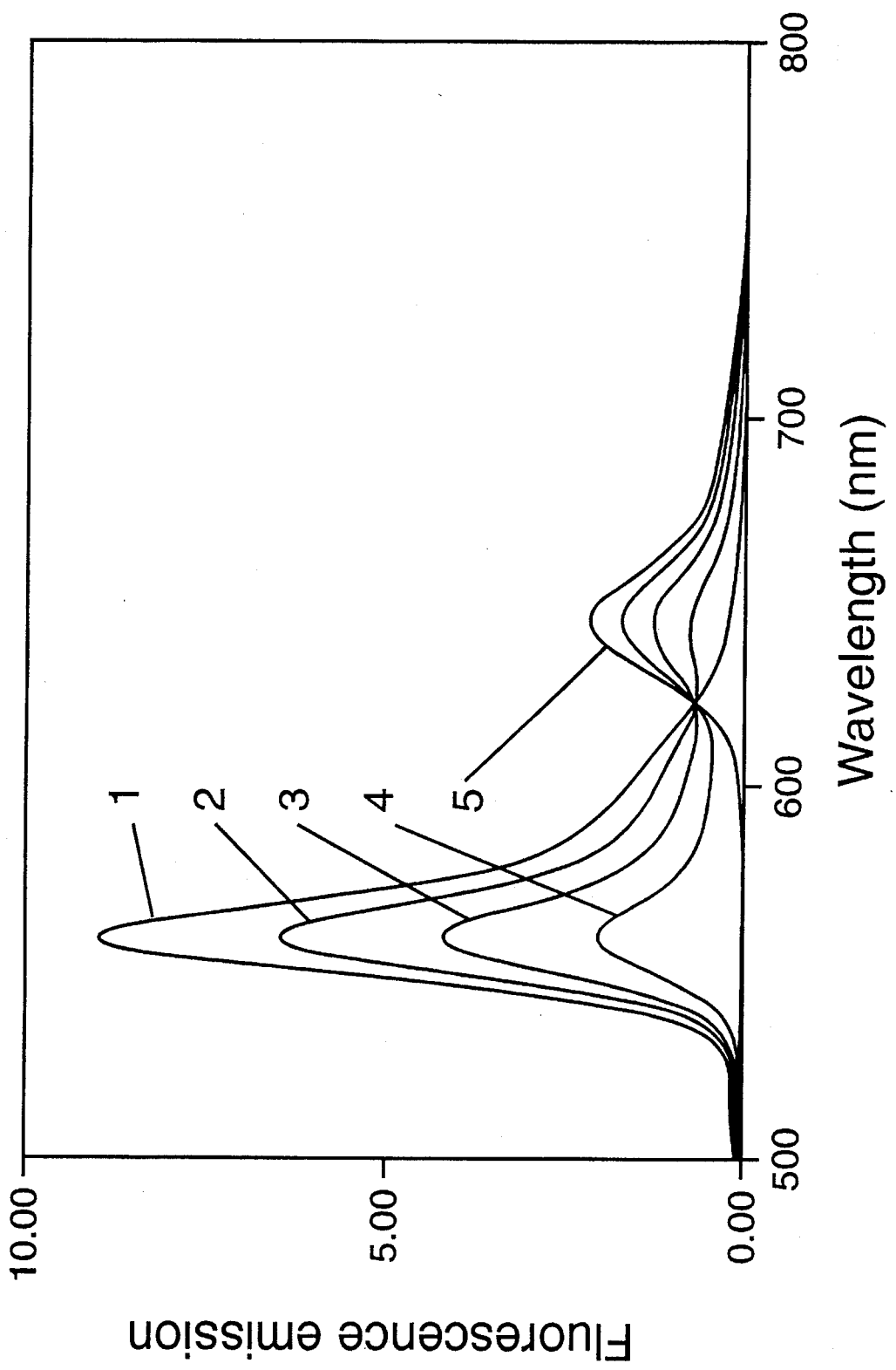
Figure 5:
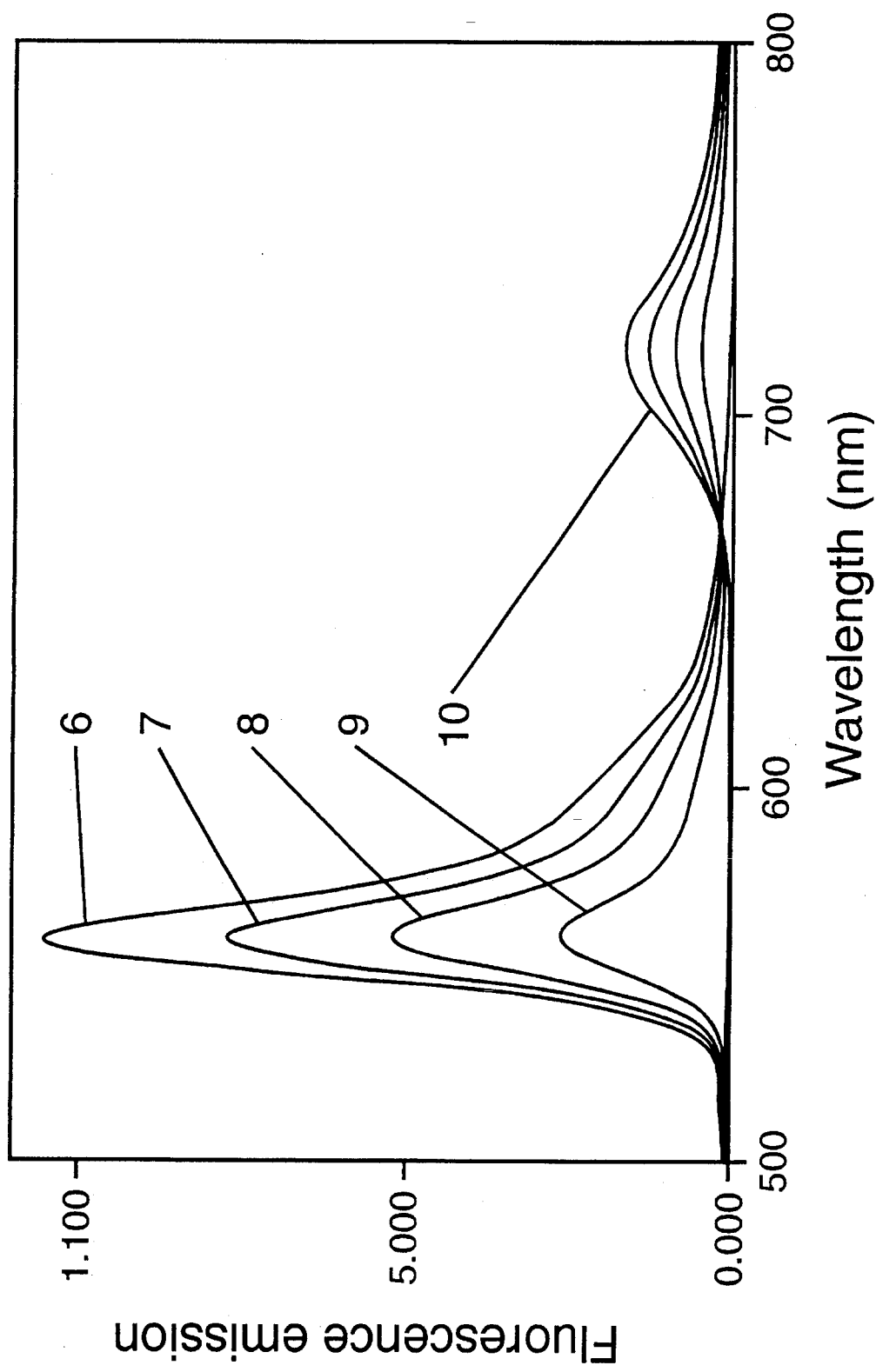
Figure 6:
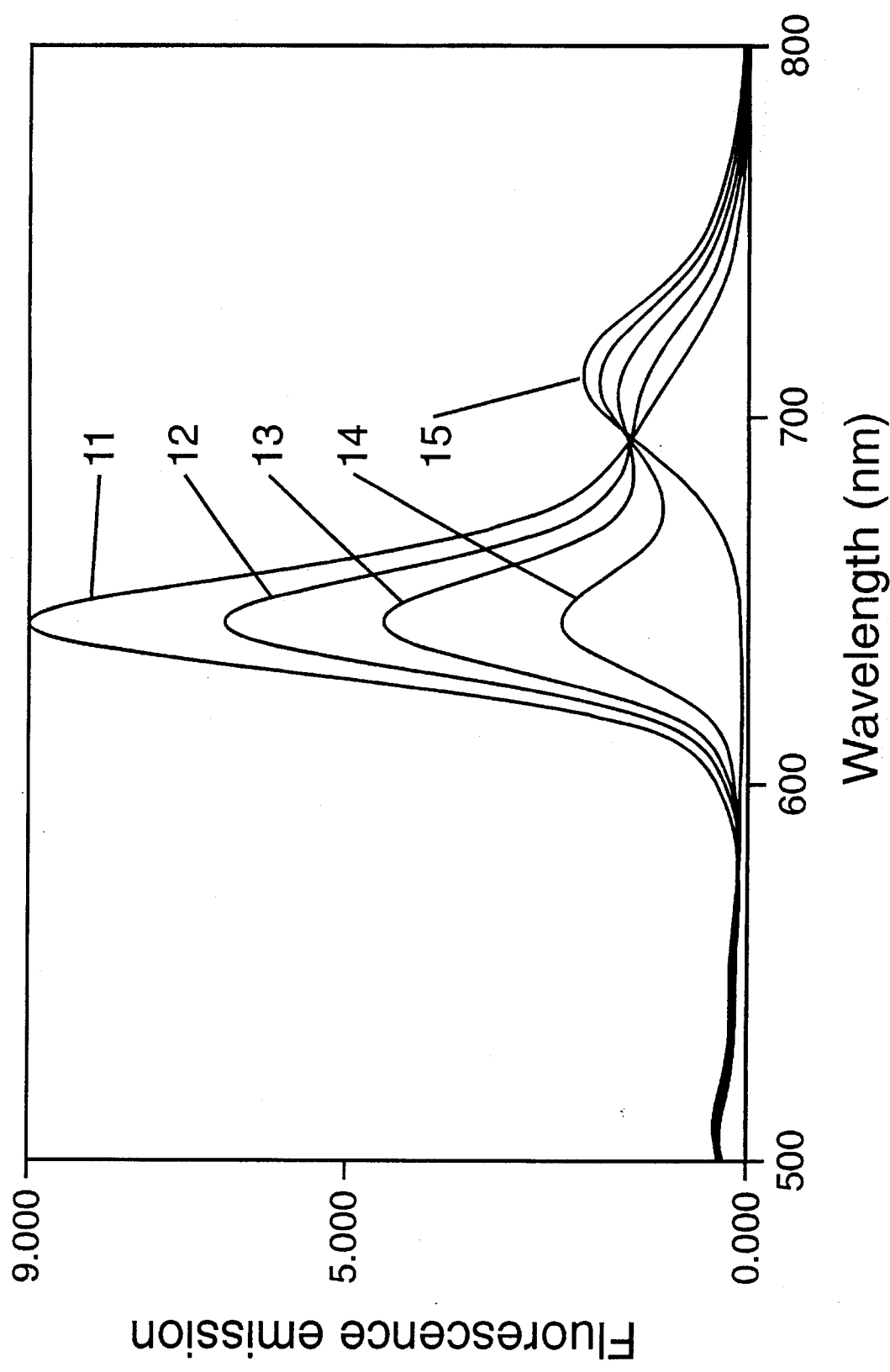

FIGS. 4–6 are graphs showing the emission spectra of the Combinatorial Mixtures according to Table 5 below.

FIG. 4 shows the emission spectra of Mixtures 1–4;

FIG. 5 shows the emission spectra of Mixtures 5–8;

FIG. 6 shows the emission spectra of Mixtures 9–12.

SUMMARY OF THE INVENTION AND DESCRIPTION OF PREFERRED EMBODIMENTS

The invention relates to methods for labeling one or more target materials using surface coated fluorescent microparticles with unique characteristics. The unique coated microparticles are combined with a sample thought to contain such material(s). Sufficient time is allowed for the coated microparticles to form a complex with the target materials. The sample is then optionally illuminated, resulting in fluorescence of the microparticles that is used to detect one or more target materials. Alternatively, the complex formed when the microparticle-labeled probes label the target materials is used as a probe for other target materials.

The unique microparticles used to practice the invention have at least two components: an external substance or coating (target complement) that is selective for each target material and an internal mixture of multiple fluorescent dyes to allow for controlled enhancement of the effective Stokes shift. The effective Stokes shift is the Stokes shift of the microparticle, i.e. the difference between the peak excitation wavelength of the initial donor dye and the peak emission wavelength of the ultimate acceptor dye after incorporation in the microparticle.

Selection of Dyes

The invention utilizes coated microparticles that contain a series of two or more fluorescent compounds having overlapping excitation and emission spectra. Efficient energy transfer from the excitation wavelength of the first dye in the series which is re-emitted at the emission wavelength of last dye in the series results in a large and readily controllable effective Stokes shift. Selection of appropriate dyes results in fluorescent probes with desired excitation and/or emission wavelengths and preselected and increased effective Stokes shift.

A series of fluorescent dyes is selected for incorporation into the microparticles based on their excitation and emission spectral properties. The dyes included in the series form a cascade of excitation energy transferred from high energy (short wavelength) to low energy (long wavelength) resulting in enhanced optical luminescence from the final dye in the series, regardless of the sequence of their incorporation or their random physical location in the microparticles.

The spectral properties for the series of fluorescent dyes should be determined in the polymeric materials in which they will be used. Although certain 4,4-difluoro-4-bora-3a,4a,8-triaza-s-indacene and 4,4-difluro-4-bora-3a,4a-diaza-s-indacene dyes, and dibenzo-substituted derivatives thereof, have been found to have spectral properties in polymer materials that are comparable to their spectral properties in solution, most dyes show significant and unpredictable spectral shifts depending on the media in which they are measured. Generally, oil soluble dyes and neutral dyes combine more readily with the polymeric materials. In addition to the desired excitation and emission peaks as described below, dyes useful for the invention also generally have a quantum yield of greater than about 0.2, preferably greater than about 0.5, as well as an extinction coefficient of greater than about 25,000 $cm^{-1}M^{-1}$, preferably greater than about 50,000 $cm^{-1}M^{-1}$.

The excitation and emission peaks and other spectral properties of candidate dyes are easily determined by conventional means. The excitation peak(s) of a dye can be approximately determined by running an absorption spectrum on any absorption spectrophotometer or, exactly, by running a fluorescent excitation spectrum using a scanning fluorescence spectrophotometer. The emission peak of the dye is also determined by using a fluorescence spectrophotometer to get an emission spectrum using a scanning fluorometer. Quantum yield is typically determined by measuring with a fluorometer the total fluorescence emission in the polymer of both the unknown dye and a reference dye with known absorbances at the excitation wavelength. The extinction coefficient is typically determined for a free dye in solution by using a spectrophotometer to measure absorbance of a solution with a gravimetrically determined concentration and calculating the extinction coefficient based on the Beer-Lambert law. After determining the spectral characteristics of likely dyes, dyes having the desired spectral characteristics are selected.

TABLE 1

CONVENTIONAL FLUORESCENCE EXCITATION SOURCES[a]

| Sources | Useful Wavelengths (nm) | Principal Lines (nm) |
|---|---|---|
| Mercury Arc | 250–600 | 254, 366, 436, 546 |
| Xenon Arc | 250–1000 | 467, several >800 |
| Tungsten Filament | 350–1000 | None |
| He—Cd Laser | 325, 442 | 442 |
| Ar Laser | 350, 360, 458, 476, 488, 496, 514 | 488, 514 |
| He—Ne Laser | 543, 594, 633 | 633 |
| Kr Laser | 530, 568, 647, 676 | 647 |
| Diode Laser | >650 | 850 (GaAlAs)[b] |

[a]Only primary excitation sources capable of continuous operation (CW) have been considered. Several other laser sources are available that either provide pulsed output (e.g. $N_2$ laser) or require pumping by CW ion lasers (e.g. dye lasers, Ti:Sapphire lasers).
[b]Material dependent, multiple types available.

The series of fluorescent dyes contains an initial donor dye with a desired excitation peak. The initial donor dye receives external excitation energy, such as from photons, x-rays, or decay of radioactive materials (e.g. β-emitters). In one embodiment of the invention, the initial donor dye receives excitation energy from incandescent or laser-based excitation sources to avoid the hazards of radioactive materials. Lasers, including argon ion, krypton ion, He—Cd, He—Ne, excimer, diode, metal vapor, neodymium-YAG, nitrogen and others, produce from one to several discrete lines that contain sufficient power for fluorescence excitation. Laser sources are available to provide many excitation lines over the spectrum from the UV to the infrared, to excite a wide range of fluorescent dyes.

The initial donor dye in the series has an excitation peak that overlaps the emission wavelength of energy from a preferred excitation source. For example, the most widely used beam-scanning confocal microscopes currently use air cooled Ar ion lasers, or more recently Ar—Kr gas mixes, allowing for fluorescent dye excitation between about 450 and 650 nm. Preferably, the excitation peak is optimal for absorption of energy from the excitation source, i.e. the excitation peak significantly overlaps the output of the excitation source. Table 1 lists the wavelengths for a number of conventional excitation sources.

The series of fluorescent dyes used for the invention also has an ultimate acceptor dye with a desired emission peak. Generally, the desired emission peak is based on the magnitude of effective Stokes shift desired. The intensity of the fluorescence emission with respect to background "noise" (the signal-to-noise ratio), is fundamental to sensitivity and image contrast. The signal-to-noise quality of fluorescence data may be severely compromised by background signals at wavelengths different than the emitted fluorescence of interest. The background signals may result from light scatter or may be due to fluorescence intrinsically present in many biological systems or generated from an analytically useful second emitting species. It is possible, for example, to avoid cellular autofluorescence or to provide for a range of materials that can be excited by a common wavelength but detected at different wavelengths by selection of a dye series that gives the desired effective Stokes shift.

Figure 1:
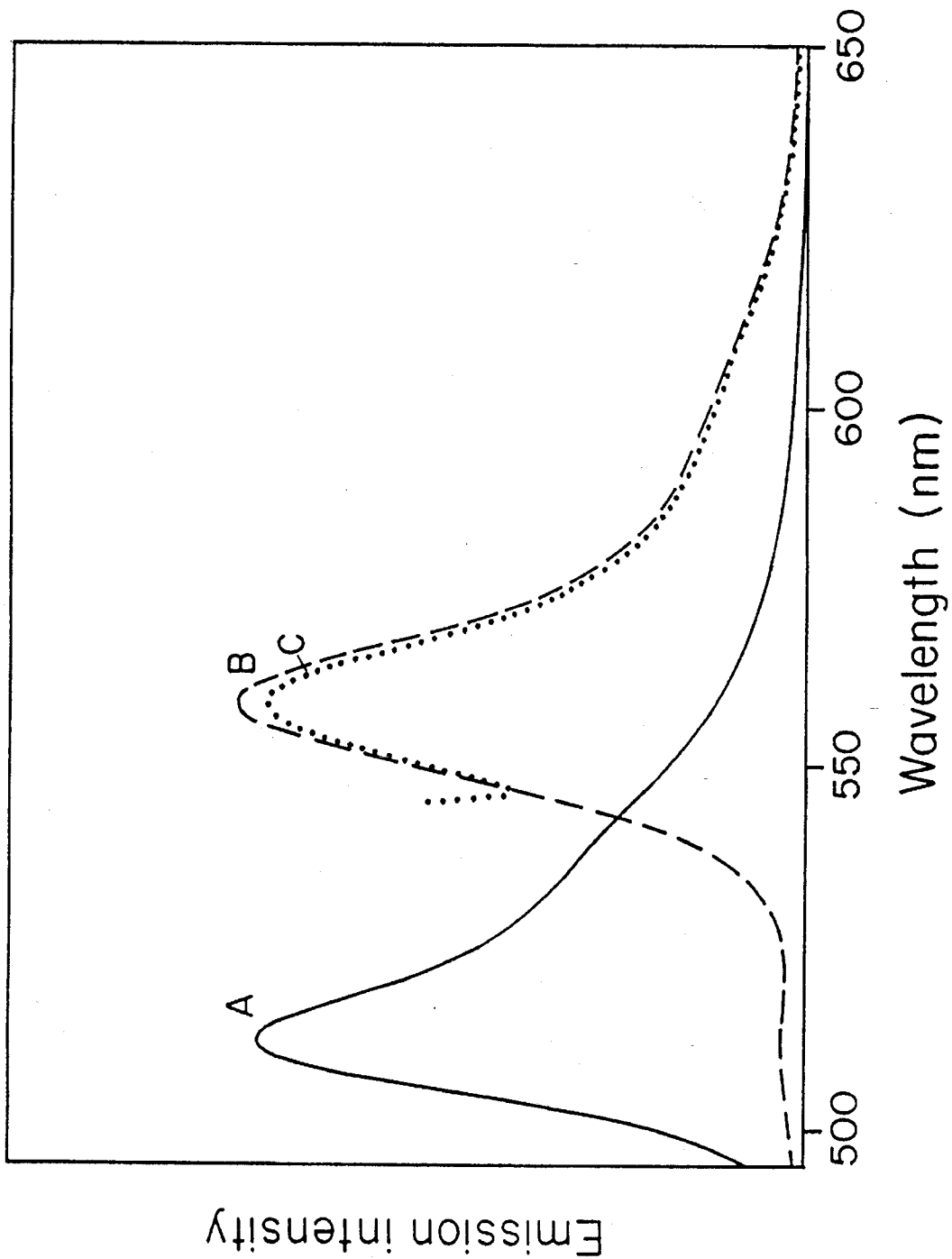
FIG. 1 is a graph comparing the emission spectra of 0.093 micrometer polystyrene latex particles containing polyazaindacene dyes and dye combinations. Spectrum A represents 16 µMol/g-latex of Compound 1 (see Table 2 below), excited at 490 nm (a preferred excitation wavelength); Spectrum B results from particles containing a mixture of 16 µMol/g-latex of Compound 1 (donor) and 9.6 µMol/g of Compound 3 (acceptor), also excited at 490 nm; spectrum C is the emission of particles containing 9.6 µMol/g-latex of Compound 3, excited at 540 nm.
Figure 3:
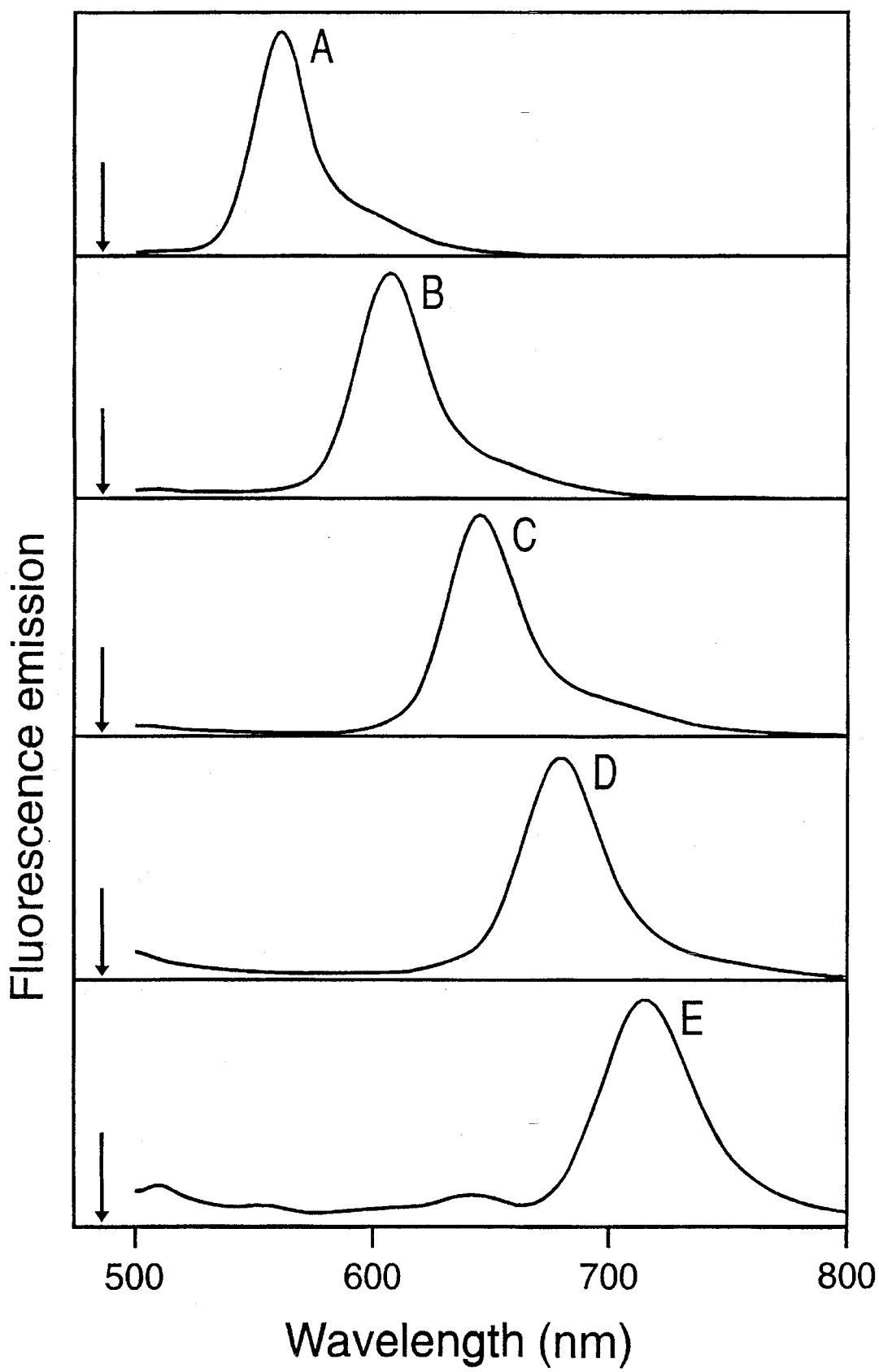
FIG. 3 is a graph comparing the normalized emission spectra of 0.01 micrometer latex microparticles with different combinations of polyazaindacene dyes (from Table 2 below) demonstrating a range of excitation maximum (nm)/emission maximum (nm) pairs. The arrow in each spectrum represents the 488 nm spectral line of the argon laser.

The desired magnitude of effective Stokes shift may require that additional or "transfer" dyes be included in the series of fluorescent dyes to act as both intermediate donor and acceptor dyes. Individual dyes having a relatively narrow Stokes shift are preferred as transfer dyes for ease of exactly tailoring the desired excitation and emission peaks. Each transfer dye receives energy from the preceding dye in the series (acting as an acceptor dye with respect to the preceding dye) and substantially transfers the received energy to the next dye in the series (acting as a donor dye with respect to the next dye). Each dye in the series of fluorescent dyes has spectral overlap with the other dyes in the series, i.e. the emission peak of each donor or transfer dye in the series overlaps the excitation peak of the following acceptor or transfer dye in the series (Ex. 4/FIG. 3). The excitation and emission peaks overlap sufficiently so that, upon excitation, significant (i.e., greater than about 50%) transfer of the excitation energy from each dye to the next is achieved. The efficiency of energy transfer is measured by the loss in fluorescence intensity of the emission peak of the donor dye measured at the same degree of dye loading as polymer loaded with only the donor dye (FIG. 1). Typically, substantially complete energy transfer is achieved (i.e. greater than about 90%). Preferably, greater than about 95% energy transfer is achieved. More preferably, greater than about 98% energy transfer is achieved. Addition of a transfer dye is most appropriate when the efficiency of energy transfer falls below about 90%. The function of the transfer dye is to accept the excited state energy from the initially excited donor dye and to facilitate transfer of this energy to the ultimately detected acceptor dye.

Typically, the desired energy transfer is achieved when sufficient amounts of dyes are loaded into the polymeric microparticles so that the average intermolecular distance between donor and transfer and/or acceptor dyes is between about 40 Å and about 25 Å. Intermolecular distances between the dyes of greater than about 40 Å generally result in less efficient energy transfer, while intermolecular distances between the dyes of less than about 25 Å generally result in non-radiative energy loss that reduces the fluorescence emission of the dyes.

A sufficient number of donor, acceptor and transfer dyes are included in the series so that efficient energy transfer from the initial dye in the series to the ultimate dye in the series occurs. Although the dyes may be included in equal amounts, too much total dye may result in deterioration in properties of the polymer and in suboptimal fluorescence of the materials because of non-radiative energy loss. The average random distance between the fluorophores compatible with significant energy transfer generally results when the total dye concentration is less than about 10% (w/w); preferably the total dye concentration is between about 0.5 and 2% (w/w); more preferably between about 0.8 and 1.2% (w/w). Less (fewer molar equivalents) transfer dye than donor and acceptor dyes may sometimes be used to achieve the desired energy transfer. Less (fewer molar equivalents) ultimate acceptor dye than initial donor dye may also be effective in achieving the desired energy transfer. Increasing the amount of ultimate acceptor in proportion to the amount of initial donor generally has little effect on improving the ultimate fluorescent signal, whereas increasing the proportion of initial donor improves the effective extinction coefficient of the microparticles and leads to greater emission from the ultimate acceptor dye. While not wishing to be bound by theory, it appears that the donor dye functions as a radiation collection mechanism for funneling energy output to the acceptor dye such that more initial donor dye results in more efficient absorption at excitation which in turn yields a more intense fluorescence signal. A workable ratio of initial donor dye to ultimate acceptor dye is between about 1:5 and about 10:1; preferably between about 1:1 and about 8:1.

In one embodiment of the invention, novel fluorescent materials are prepared from two or more indacene dyes, including polyazaindacene dyes (i.e. derivatives of 4,4-difluoro-4-bora-3a,4a-diaza-s-indacene or 4,4-difluoro-4-bora-3a,4a,8-triaza-s-indacene, or 4,4-difluoro-4-bora-3a, 4a-diaza-dibenz-s-indacene). Polyazaindacene derivatives suitable for preparation of fluorescent polymer microparticles according to this invention have the general structure of formula (I):

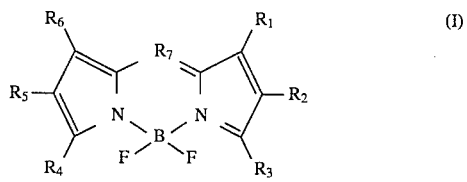

where $R_7$ is nitrogen; methine; or halogen-, cyano-, alkyl-, perfluoroalkyl-, alkoxy-, alkenyl-, alkynyl-, cycloalkyl-, arylalkyl-, acyl-, aryl- or heteroaryl-substituted methine. Substituents $R_1$–$R_6$, which may be the same or different, are hydrogen, halogen, nitro, cyano, alkyl, perfluoroalkyl, alkoxy, alkenyl, alkynyl, cycloalkyl, arylalkyl, acyl, or substituted or unsubstituted aryl or heteroaryl, alone or in combination.

Alternatively, $R_7$ is methine; or alkyl-, perfluoroalkyl-, cycloalkyl-, aryl- or heteroaryl-substituted methine; and adjacent substituents $R_1$–$R_2$, and $R_5$–$R_6$, each combine to form a fused benzo ring according to the formula (II):

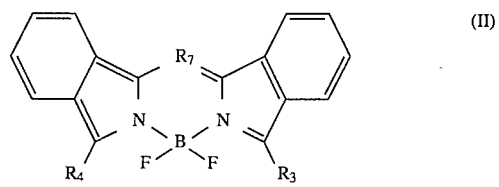

Each fused benzo ring optionally contains one or more additional substituents, which may be the same or different, that are hydrogen, halogen, nitro, cyano, alkyl, perfluoroalkyl, alkoxy, alkenyl, alkynyl, cycloalkyl, alkylthio, alkylamido, amino, monoalkylamino, dialkylamino, or substituted or unsubstituted aryl, heteroaryl, aryl-amido, heteroaryl-amido, aryl-oxy, heteroaryl-oxy, aryl-amino, or heteroaryl-amino, or 1–2 additional fuzed benzo or heteroaromatic rings that are optionally substituted or unsubstituted. Preferably, the dibenzo-substituted dyes contain substituents at $R_3$ and $R_4$ that are other than hydrogen.

The alkyl, cycloalkyl, arylalkyl, acyl, alkoxy, perfluoroalkyl, alkylthio, alkylamido, arylamido, heteroarylamido, amino, monoalkylamino, dialkylamino, alkenyl, and alkynyl substituents of the polyazaindacene derivatives generally each have independently fewer than about 20 carbon atoms, preferably fewer than about 10 carbon atoms (cycloalkyl preferably fewer than 7). The term alkenyl includes ethenyl or conjugated dienyl or trienyl, which may be further substituted by hydrogen, halogen, alkyl, cycloalkyl, arylalkyl, acyl, (the alkyl portions of which each contain fewer than about 20 carbons), cyano, carboxylate ester, carboxamide, aryl or heteroaryl.

A heteroaryl group is a heterocyclic aromatic group that contains at least one heteroatom (a non-carbon atom forming the ring structure). The heteroaryl group can be a single ring structure or a fused two- or three-ring structure. Each ring can be a 5- or 6-member ring. The heteroaryl group can contain one or more heteroatoms. The term heteroaryl includes its alkyl-, aryl-, arylalkyl- or heteroaryl-substituted derivatives. For example, the heteroaryl substituent is pyrrole, thiophene, or furan (single ring, single heteroatom), or oxazole, isoxazole, oxadiazole, or imidazole (single ring, multiple heteroatoms). Alternatively, the heteroaryl group is a multi-ring structure containing one or more heteroatoms, for example, the heteroaryl substituent is benzoxazole, benzothiazole, or benzimidazole, (multi-ring, multiple heteroatoms), or benzofuran or indole (multi-ring, single heteroatom).

In general, 4,4-difluoro-4-bora-3a,4a-diaza-s-indacene derivative dyes are prepared from suitable pyrrole precursors, according to methods known in the art (e.g. U.S. Pat. No. 4,916,711 to Boyer, et al. (1990) and U.S. Pat. No. 4,774,339 to Haugland, et al. (1988) each of which are incorporated by reference). Typically, approximately stoichiometric proportions of pyrrole precursors, one of which contains an aldehyde or ketone function in the 2-position, are condensed in a reaction mediated by a suitable acid, such as hydrogen bromide, to yield an intermediate pyrromethene salt. Cyclization of the heterocyclic ring formation is completed by addition of boron trifluoride in combination with a strong base such as trimethylamine. Derivatives of 4,4-difluoro-4-bora-3a,4a,8-triaza-s-indacene are synthesized by the cyclization of azapyrromethenes with boron trifluoride in the presence of a base such as N,N-diisopropylethylamine. The azapyrromethene intermediates are prepared by the acid catalyzed condensation of 2-nitrosopyrrole derivatives with suitable pyrrole precursors having a hydrogen on the 2-position. The 4,4-difluoro-4-bora-3a,4a-diaza-dibenz-s-indacene derivative dyes are prepared according yet another synthetic scheme. Initially, a dibenzopyrromethene intermediate is prepared by the condensation of two appropriately substituted 2-acylacetophenones in the presence of an ammonium salt. For a non-hydrogen substituted methine at $R^7$, dibenzopyrromethene intermediates are prepared by heating an appropriately substituted hydrindenone with aqueous ammonia in a sealed tube. In either case, treatment of a dibenzopyrromethene intermediates with a source of $BF_3$ yields dibenzopyrrometheneboron difluoride dyes.

A representative, non-exclusive sample of polyazaindacene dyes suitable for preparing fluorescent microparticles with controlled effective Stokes shifts in listed in Table 2 and a summary of their spectral properties in organic solvent and in microparticles is included in Table 3. Other useful dipyrrometheneboron difluoride dyes are described in U.S. Pat. Nos. 5,187,288 to Kang, et al., issued Feb. 2, 1993 and 5,248,782 to Haugland, et al., issued Sep. 9, 1993; and co-pending application DIBENZOPYROMETHENEBORON DIFLUORIDE DYES, filed May 20, 1994 by inventors Kang and Haugland (each of which documents is incorporated by reference).

tions of donor, transfer and/or acceptor dyes; and 4) the average distance between the dye molecules.

Utilizing both the excitation and emission properties, the fluorescent materials are easily tailored to meet the specific requirements of the excitation source and the detector for a specific application. For example, Compound 1 may be selected as the donor dye having a very useful excitation of around 488 nm corresponding to the principle emission of argon lasers, with other dyes in Table 2 selected as transfer or acceptor dyes to yield a desired emission peak.

Polystyrene microparticles labeled only with Compound 2 have maximum excitation at 504 nm and yellow-green fluorescence emission centered at about 512 nm. When the particles are labeled only with Compound 3, they have orange fluorescence emission centered at 557 nm. When Compound 2 (donor) and Compound 3 (acceptor) are combined in the appropriate molar ratios and incorporated into polystyrene microparticles (Ex. 3), the yellow-green emission of Compound 2 at 5 12 nm is transferred with greater than about 95% efficiency to Compound 3, resulting in orange emission at 557 nm. The effective Stokes shift is increased from 8 nm to 56 nm (FIG. 1). Transfer dyes can be added to further increase the effective Stokes shift. When

TABLE 2

REPRESENTATIVE POLYAZAINDACENE DYES COMBINED IN MICROPARTICLES

| Compound | $R_1$ | $R_2$ | $R_3$ | $R_4$ | $R_5$ | $R_6$ | $R_7$ |
|---|---|---|---|---|---|---|---|
| 1 | H | H | H | $CH_3$ | H | $CH_3$ | CH |
| 2 | $CH_3$ | H | $CH_3$ | $CH_3$ | H | $CH_3$ | CH |
| 3 | $CH_3$ | H | $CH_3$ | Ph | H | Ph | CH |
| 4 | Ph | H | Ph | Ph | H | Ph | CH |
| 5 | Ph | H | Ph | Ph | H | Ph | N |
| 6 | Ph | H | Ph | 2-pyrrolyl | H | H | CH |
| 7 | $CH_3O$-(phenyl) | | 4-methoxyphenyl | 4-methoxyphenyl | | (phenyl)-$OCH_3$ | CH |

TABLE 3

SPECTRA OF REPRESENTATIVE POLYAZAINDACENE DYES

| Compound | $\lambda^{Abs}_{max}$ (nm)† | $\lambda^{Em}_{max}$ (nm)† | $\lambda^{Abs}_{max}$ (nm)‡ | $\lambda^{Em}_{max}$ (nm)‡ |
|---|---|---|---|---|
| 1 | 490 | 509 | 495 | 515 |
| 2 | 505 | 515 | 504 | 512 |
| 3 | 528 | 548 | 540 | 557 |
| 4 | 564 | 591 | 578 | 605 |
| 5 | 644 | 668 | 650 | 679 |
| 6 | 606 | 633 | 625 | 645 |
| 7 | 673 | 704 | 685 | 720 |

†Absorption maxima ($\lambda^{Abs}_{max}$) and emission maxima ($\lambda^{Em}_{max}$) measurements of free dye in methanol.
‡Absorption maxima ($\lambda^{Abs}_{max}$) and emission maxima ($\lambda^{Em}_{max}$) measurements of dye in aqueous suspension of latex. Optical density set at 0.1 at 700 nm or 800 for the longest wavelength.

Appropriate selection of polyazaindacene derivatives, when incorporated together into a polymeric microparticle, have desired excitation and emission wavelengths that overlap sufficiently so that efficient transfer of energy from donor to acceptor is achieved, considering 1) the wavelength of the excitation and emission of the donor, transfer and/or acceptor dyes; 2) the overlap of the donor dye emission with the transfer and/or acceptor excitation; 3) relative concentra- Compound 2 (donor), Compound 3 (transfer dye) and Compound 4 (acceptor) are combined in the appropriate molar ratios and incorporated into latex microparticles (Ex. 4), energy transfer (with greater than about 95% efficiency) results in red emission at 605 nm. The effective Stokes shift is increased from 8 nm to 101 nm (compare FIG. 3; Spectrum B). When Compound 2 (initial donor), Compound 3 (transfer dye), Compound 4 (transfer dye) and Compound 6 (ultimate acceptor) are combined and incorporated into latex microparticles, energy transfer (with greater than about 90% efficiency) results in dark red emission at 645 nm. The effective Stokes shift is increased from 8 nm to 141 nm (compare FIG. 3; Spectrum C). When Compound 5 is added as the ultimate acceptor dye (Compound 6 becomes a transfer dye), energy transfer results in an emission maximum at 679 nm and the effective Stokes shift is increased to 191 nm (compare FIG. 3; Spectrum D). The addition of Compound 7 as the ultimate acceptor dye results in an emission maximum at 720 nm and the effective Stokes shift is increased to 232 nm (compare FIG. 3; Spectrum E). The spectra in FIG. 3 result from microparticles containing Compound 1 as the initial donor dye.

Alternatively, Compound 3 can be used as the donor and Compound 4 as the acceptor, resulting in latex particles that can be excited at about 530 nm and that emit at about 605 nm (an effective Stokes shift of about 75 nm), once again using the common argon laser (secondary line) but avoiding most of the autofluorescence of human serum. As long as there is spectral overlap between emission and excitation peaks of the dyes, many other dye combinations are possible.

In an another embodiment of the invention, the fluorescent dyes are a series of coumarin dyes. Suitable dyes include the commercially available dyes listed in Table 4. As with the polyazaindacene dyes previously described, an appropriate series of coumarin derivatives can be selected, which when incorporated together into a polymeric microparticle, have desired excitation and emission wavelengths that overlap sufficiently so that efficient transfer of energy from donor to acceptor is achieved. For example, when initial donor Coumarin 138 (7-Dimethylaminocyclopenta[c]coumarin), with excitation at 360 nm and emission centered at about 415 nm (in polystyrene latex) is combined in the appropriate molar ratio with ultimate acceptor Coumarin 314 (2,3,5,6-1H,4H-Tetrahydro-9-carboethoxyquinolizino-(9,9a,1-gh)coumarin), with absorption at 430 nm and emission centered at about 460 nm (in polystyrene latex) and incorporated into latex microparticles (Ex. 5), the blue emission of the Coumarin 138 is transferred to the Coumarin 314, resulting in blue-green emission centered at about 460 nm. The effective Stokes shift is increased from 55 nm to 100 nm.

The novel microparticles have very high fluorescence efficiency, typically with no apparent loss of signal intensity through the intermolecular energy transfer process. For example, excitation of the donor dye in the fluorescent microparticles illustrated in FIG. 1 at 490 nm, where the absorbance is 0.58 gives a signal at 557 nm that is equal to the corresponding signal at 557 nm resulting from excitation of the acceptor dye at 540 nm, where the absorbance is also 0.58. This extremely high efficiency of transfer is consistent with the observation that there is almost no emission signal detectable from the donor dye in the fluorescence spectrum of FIG. 1. Comparison of the integrated area of the emission signal of from 490 nm to 520 nm of Spectrum A, FIG. 1 with the integrated area of the emission signal from 490 nm to 520 nm of Spectrum B, FIG. 1 indicates that the transfer efficiency is about 99%.

The degree of overlap between the emission peak of the donor dye and the excitation peak of the transfer and/or acceptor dye(s) does not have to be complete. For example, in microspheres where there is less than complete overlap between the emission peak of diphenylhexatriene (DPH) and the excitation peak of Compound 1, this overlap, nevertheless, results in transfer of about 75% of the emission from DPH to Compound 1. By adjusting the concentration of dyes, energy transfer of close to 100% is possible.

Typically, the dyes are selected from the same family, such as the polyazaindacenes or coumarins described above. Other suitable families of dyes include hydrocarbon and substituted hydrocarbon dyes; scintillation dyes (usually oxazoles and oxadiazoles); aryl- and heteroaryl-substituted polyolefins ($C_2$–$C_8$ olefin portion); carbocyanines; phthalocyanines; oxazines; carbostyryl; and porphyrin dyes (see Table 4). It is also possible, however, to achieve efficient energy transfer between different classes of dyes (dyes that are structurally different) such as between polyolefinic dyes and dipyrrometheneboron difluoride dyes (Ex. 6); coumarin dyes and dipyrrometheneboron difluoride dyes (Ex. 7); polyolefinic dyes and coumarin dyes; dipyrrometheneboron difluoride dyes and oxazine dyes; and many others. Table 3 contains a partial list of commercially available, suitable fluorescent dyes. Potentially any fluorescent dye that is sufficiently soluble (typically >0.01% by weight) in the particle can be used.

TABLE 4: COMMERCIALLY AVAILABLE DYES

5-Amino-9-diethyliminobenzo(a)phenoxazonium Perchlorate
7-Amino-4-methylcarbostyryl
7-Amino-4-methylcoumarin
7-Amino-4-trifluoromethylcoumarin
3-(2'-Benzimidazolyl)-7-N,N-diethylaminocoumarin
3-(2'-Benzothiazolyl)-7-diethylaminocoumarin
2-(4-Biphenylyl)-5-(4-t-butylphenyl)-1,3,4-oxadiazole
2-(4-Biphenylyl)-5-phenyl-1,3,4-oxadiazole
2-(4-Biphenyl)-6-phenylbenzoxazole-1,3
2,5-Bis-(4-biphenylyl)-1,3,4-oxadiazole
2,5-Bis-(4-biphenylyl)-oxazole
4,4'''-Bis-(2-butyloctyloxy)-p-quaterphenyl
p-Bis(o-methylstyryl)-benzene
5,9-Diaminobenzo(a)phenoxazonium Perchlorate
4-Dicyanomethylene-2-methyl-6-(p-dimethylaminostyryl)-4H-pyran
1,1'-Diethyl-2,2'-carbocyanine Iodide
1,1'-Diethyl-4,4'-carbocyanine Iodide
3,3'-Diethyl-4,4',5,5'-dibenzothiatricarbocyanine Iodide
1,1'-Diethyl-4,4'-dicarbocyanine Iodide
1,1'-Diethyl-2,2'-dicarbocyanine Iodide
3,3'-Diethyl-9,11-neopentylenethiatricarbocyanine Iodide
1,3'-Diethyl-4,2'-quinolyloxacarbocyanine Iodide
1,3'-Diethyl-4,2'-quinolylthiacarbocyanine Iodide
3-Diethylamino-7-diethyliminophenoxazonium Perchlorate
7-Diethylamino-4-methylcoumarin
7-Diethylamino-4-trifluoromethylcoumarin
7-Diethylaminocoumarin
3,3'-Diethyloxadicarbocyanine Iodide
3,3'-Diethylthiacarbocyanine Iodide
3,3'-Diethylthiadicarbocyanine Iodide
3,3'-Diethylthiatricarbocyanine Iodide
4,6-Dimethyl-7-ethylaminocoumarin
2,2'''-Dimethyl-p-quaterphenyl
2,2''-Dimethyl-p-terphenyl
7-Dimethylamino-1-methyl-4-methoxy-8-azaquinolone-2
7-Dimethylamino-4-methylquinolone-2
7-Dimethylamino-4-trifluoromethylcoumarin
2-(4-(4-Dimethylaminophenyl)-1,3-butadienyl)-3-ethylbenzothiazolium Perchlorate
2-(6-(p-Dimethylaminophenyl)-2,4-neopentylene-1,3,5-hexatrienyl)-3-methylbenzothiazolium Perchlorate
2-(4-(p-Dimethylaminophenyl)-1,3-butadienyl)-1,3,3-trimethyl-3H-indolium Perchlorate
3,3'-Dimethyloxatricarbocyanine Iodide
2,5-Diphenylfuran
2,5-Diphenyloxazole
4,4'-Diphenylstilbene
1-Ethyl-4-(4-(p-Dimethylaminophenyl)-1,3-butadienyl)-pyridinium Perchlorate
1-Ethyl-2-(4-(p-Dimethylaminophenyl)-1,3-butadienyl)-pyridinium Perchlorate
1-Ethyl-4-(4-(p-Dimethylaminophenyl)-1,3-butadienyl)-quinolium Perchlorate
3-Ethylamino-7-ethylimino-2,8-dimethylphenoxazin-5-ium Perchlorate
9-Ethylamino-5-ethylamino-10-methyl-5H-benzo(a)phenoxazonium Perchlorate
7-Ethylamino-6-methyl-4-trifluoromethylcoumarin
7-Ethylamino-4-trifluoromethylcoumarin
1,1',3,3,3',3'-Hexamethyl-4,4',5,5'-dibenzo-2,2'-indotricarbocyanine Iodide
1,1',3,3,3',3'-Hexamethylindodicarbocyanine Iodide
1,1',3,3,3',3'-Hexamethylindotricarbocyanine Iodide
2-Methyl-5-t-butyl-p-quaterphenyl N-Methyl-4-trifluoromethylpiperidino-<3,2-g>coumarin
3-(2'-N-Methylbenzimidazolyl)-7-N,N-diethylaminocoumarin
2-(1-Naphthyl)-5-phenyloxazole
2,2'-p-Phenylen-bis(5-phenyloxazole)
3,5,3"",5""-Tetra-t-butyl-p-sexiphenyl
3,5,3"",5""-Tetra-t-butyl-p-quinquephenyl
2,3,5,6-1H,4H-Tetrahydro-9-acetylquinolizino-<9,9a,1-gh>coumarin
2,3,5,6-1H,4H-Tetrahydro-9-carboethoxyquinolizino-<9,9a,1-gh>coumarin
2,3,5,6-1H,4H-Tetrahydro-8-methylquinolizino-<9,9a,1-gh>coumarin
2,3,5,6-1H,4H-Tetrahydro-9-(3-pyridyl)-quinolizino-<9,9a,1-gh>coumarin
2,3,5,6-1H,4H-Tetrahydro-8-trifluoromethylquinolizino-<9,9a,1-gh>coumarin
2,3,5,6-1H,4H-Tetrahydroquinolizino-<9,9a,1-gh>coumarin
3,3',2",3'"-Tetramethyl-p-quaterphenyl
2,5,2"",5""-Tetramethyl-p-quinquephenyl
P-terphenyl
P-quaterphenyl
Nile Red
Rhodamine 700
Oxazine 750
Rhodamine 800
IR 125
IR 144
IR 140
IR 132
IR 26
IR 5
Diphenylhexatriene
Diphenylbutadiene
Tetraphenylbutadiene
Naphthalene
Anthracene
Pyrene
Chrysene
Rubrene
Coronene
Phenanthrene
Fluorene
Aluminum phthalocyanine
Platinum octaethylporphyrin Once the spectral characteristics of a dye are determined in polymeric materials, as described above, those characteristics can be used to select the optimal dye series for a given application, taking into account the excitation source to be used, the available detection system, and the environment in which the materials will be used.

Incorporation Into Microparticle

After selection of the series of dyes with the desired spectral characteristics, the dyes are incorporated in a polymeric microparticle. The polymeric microparticle can be prepared from a variety of polymerizable monomers, including styrenes, acrylates and unsaturated chlorides, esters, acetates, amides and alcohols, including, but not limited to polystyrene (including high density polystyrene latexes such as brominated polystyrene), polymethylmethacrylate and other polyacrylic acids, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidene chloride, and polydivinylbenzene. Typically the microparticles are prepared from latex monomers.

In one embodiment of the invention, the novel fluorescent materials are prepared from undyed microparticles. The microparticles can be manufactured in a variety of useful sizes and shapes, generally less than about 50 micrometers in diameter. They may be spherical or irregular in shape. Typically, the labeled microparticles are between about 0.01 micrometers and about 50 micrometers in diameter and are spherical. More typically the microparticle is a microsphere less than about 15 micrometers in diameter. The microparticles may be of uniform size and/or shape or non-uniform. Alternatively, one or more dyes are added to pre-dyed microparticles such as the many varieties of fluorescent microspheres available commercially, provided that the requirement for spectral overlap between the resident dye and the additional dye(s) is met.

The fluorescent dyes are incorporated into the microparticles by any of the methods known in the art, such as copolymerization of a monomer and a dye-containing comonomer or addition of a suitable dye derivative in a suitable organic solvent to an aqueous suspension of polymer microparticles. For example, the fluorescent microparticles can be produced by free radical-initiated, anaerobic copolymerization of an aqueous suspension of a mono-unsaturated monomer that may or may not contain a covalent bonding group such as carboxyl, amino or hydroxyl and a fluorescent monomer mixture containing at least 10% by weight of monomers comprising the appropriate mixture of donor, transfer and/or acceptor dye moieties, according to the method of Rembaum (U.S. Pat. No. 4,326,008 (1982) incorporated by reference). The fluorescent microparticles can also be produced by gradual addition of a solution of the appropriate fluorescent dyes in an appropriate solvent to a stirred aqueous suspension of microparticles, as described by Bangs (UNIFORM LATEX PARTICLES (1984, Seragen, Inc.).

A major advantage of the subject microparticles is the ability to simply mix multiple transfer dyes with an initial donor dye and an ultimate acceptor dye to increase the effective Stokes shift of the microparticles and thus tailor the microparticles to meet specific applications. This cannot readily be accomplished by chemical means such as covalent attachment of the dyes to each other. In addition, the dyes are distributed throughout the particle, at concentrations that result in intermolecular separations that are smaller than can be practically attained by covalent chemical attachment, thus improving the likelihood of energy transfer. Furthermore, the dyes reside in a polymer that appears to restrict their free movement and prevent the dye molecules from vibrationally inactivating one another. Furthermore, incorporation of dyes in the polymeric microparticles usually increases their stability to illumination and protects the dyes from components in the medium surrounding the microparticles.

Oil-soluble fluorescent dyes, being freely soluble in organic solvents and very sparingly soluble in water, can easily be introduced by solvent-based addition of the dye to previously manufactured polymer microparticles. This offers the great advantage of being able to prepare uniform polymer microparticles with desired properties by carefully optimized procedures and then later adding the fluorescent dye series of choice. Furthermore, the solvent-based addition process gives great flexibility in adjusting the relative concentrations of the dyes, a key parameter in attaining efficient energy transfer.

In this manner, a large batch of microparticles with desired physical properties, such as size and charge density, can be prepared. Then various fluorescent dyes can be added to smaller portions of this batch resulting in subbatches of fluorescent polymer microparticles with desired effective Stokes shifts that give consistent and reproducible performance in applications such as development of diagnostic tests. In the case of fluorescent microparticles prepared by solvent-based addition of the dye to previously manufactured polymer microparticles, the surface properties of the subject fluorescent microparticles are not substantially different from the surface properties of the corresponding undyed microparticles. The fluorescent label in the microparticles is also not affected by changes in pH of the medium surrounding the microparticles.

Furthermore, the dyes used in the subject microparticles are not significantly removed from the microparticles by the water-based solvents that are commonly used as a suspension medium for the microparticles. For example, when aqueous suspensions of fluorescent microparticles containing Compound 4 and Compound 6 (Table 2) were subjected to temperatures of 60° C. in the presence of 0.2% sodium dodecyl sulfate, no detectable dye was extracted from the particles. When uniform microparticles are carefully prepared, the fluorescent microparticles are monodisperse in aqueous suspension. For example, 1.09 micrometer polystyrene microspheres dyed with Compound 1 and Compound 3 were shown to be monodisperse by visual observation (epifluorescence microscopy).

The fluorescent compounds that are used to prepare the subject fluorescent polymer microparticles with large and controllable effective Stokes shift are generally lipophilic and commonly carry a net neutral charge, and therefore do not contribute to or alter the charged properties of the polymer microparticles as do other fluorescent dyes such as fluorescein and rhodamine 6G, that are commonly used to prepare fluorescent microparticles. As a result, the subject fluorescent microparticles are readily modified to include a variety of surface materials.

The microparticles are optionally further modified by coating with one or more secondary polymers to alter the surface properties of the particles. In addition, the microparticles can be prepared or purchased with a variety of surface properties, with functional groups including, but not limited to sulfate, phosphate, hydroxyl, carboxyl, ester, amide, amidine, amine, sulfhydryl and aldehyde. The surface groups can be selected to give the particles desired physical characteristics such as varying degrees of hydrophilicity. Surface groups are also important for use in covalent or non-covalent binding of additional substances to the surface of the microparticles.

Surface Material as Target Complement

The microparticles used for labeling and/or detecting target materials according to the invention contains an external substance in addition to the internal mixture of fluorescent dyes, resulting in a fluorescent microparticle-labeled probe for the target material. The external substance on the microparticle (a target complement) is selective for the target material to be labeled and optionally detected. For example, nucleic acid detection generally involves probing a sample thought to contain target nucleic acids using a nucleic acid probe that contains a nucleic acid sequence that specifically recognizes the sequence of the target nucleic acids, such that the nucleic acid probe and the target nucleic acids in combination create a hybridization pair. The nucleic acid probe typically contains from greater than about 4 bases to as many as tens of thousands of bases, although probing entire chromosomes may involve millions of bases. Any of the target complements described below may be used to label the correponding target materials.

The target material is optionally a material of biological or synthetic origin that is present as a molecule or as a group of molecules, including, but not limited to, antibodies, amino acids, proteins, peptides, polypeptides, enzymes, enzyme substrates, hormones, lymphokines, metabolites, antigens, haptens, lectins, avidin, streptavidin, toxins, poisons, environmental pollutants, carbohydrates, oligosaccarides, polysaccharides, glycoproteins, glycolipids, nucleotides, oligonucleotides, nucleic acids and derivatized nucleic acids (including deoxyribo- and ribonucleic acids), DNA and RNA fragments and derivatized fragments (including single and multi-stranded fragments), natural and synthetic drugs, receptors, virus particles, bacterial particles, virus components, biological cells, cellular components (including cellular membranes and organelles), natural and synthetic lipid vesicles, polymer membranes, polymer surfaces and particles, and glass and plastic surfaces and particles. Typically the target material is present as a component or contaminant of a sample taken from a biological or environmental system.

In one aspect of the invention, the target complement coating the microparticles is a bioreactive substance. The target material is optionally a bioreactive substance also. Bioreactive substances are substances that react with or bind to molecules that are derived from a biological system, whether such molecules are naturally occurring or result from some external disturbance of the system (e.g. disease, poisoning, genetic manipulation). By way of illustration, bioreactive substances include biomolecules (i.e. molecules of biological origin including, without limitation, polymeric biomolecules such as peptides, proteins, polysaccharides, oligonucleotides, avidin, streptavidin, DNA and RNA, as well as non-polymeric biomolecules such as biotin and digoxigenin and other haptens typically having a MW less than 1000), microscopic organisms such as viruses and bacteria, and synthetic haptens (such as hormones, vitamins, or drugs). Typically the target complement or the target material or both are amino acids, peptides (including polypeptides), or proteins (larger MW than polypeptides); or are nucleotides, oligonucleotides (less than 20 bases), or nucleic acids (i.e. polymers larger than oligonucleotides, including RNA and single- and multi-stranded DNA and fragments and derivitized fragments thereof); or are carbohydrates or carbohydrate derivatives, including monosaccharides, polysaccharides, oligosaccharides, glycolipids, and glycoproteins; or are haptens (a chemical compound that is unable to elicit an immunological response unless conjugated to a larger carrier molecule), which haptens are optionally conjugated to other biomolecules; or a microscopic organisms or components of microscopic organisms. For such bioreactive substances, there are a variety of known methods for selecting useful pairs of corresponding target complements and target materials.

Where more than one material is targeted simultaneously, multiple target complements (one for each corresponding target material) are optionally included on one microparticle or on multiple microparticles. In one aspect of the invention, microparticles having detectably distinct spectral characteristics are used for each target material, with each individual microparticle being labeled with a different target complement (e.g. one microparticle-labeled probe that emits with green fluorescence is used to label or probe for one particular gene sequence and a different microparticle-labeled probe that emits with red fluorescence is used to label a different gene sequence). Alternatively, a single set of microparticles optionally contains multiple target complements so that this set of microparticle-labeled probes can form a complex with a variety of target materials (e.g. a set of green microparticle-labeled probes, each containing antibodies to several gram positive bacteria, are used to label a variety of gram positive bacteria; or a set of red microparticle-labeled probes, each directed toward a set of centromeres (or all centromeres) is used). In yet another aspect of the invention, a target complement is selected that is selective for multiple target materials (e.g. the lectin wheat germ agglutinin has been shown to be selective for gram positive bacteria in general). Target complements are selected to have the desired degree of specificity or selectivity for the intended target materials.

One or more target complements may be attached to a single fluorescent microparticle. Each target complement is optionally covalently or non-covalently bound to the surface of the microparticle, according to methods known in the art (e.g. CHEM. SOC. REV. 2, 249 (1973) and J. EXP. MED. 154, 1539 (1981)). Attaching a target complement to a microparticle is typically done using pairs of molecules that specifically recognize and bind tightly to one another, i.e. specific binding pair members (such as avidin and biotin or digoxigenin and anti-digoxigenin antibodies, for example). One member of the specific binding pair is coupled either directly (by incorporation during enzymatic or chemical synthesis or as a 5' or 3' end label) or through a linker molecule to the target complement. The other member of the specific binding pair is coupled either directly or through a linker molecule to the fluorescent microparticle. Alternatively, the target complement is covalently linked to the fluorescent microparticle without the use of intervening specific binding pair members according to methods known in the art (e.g. Kremsky, et al., NUCLEIC ACIDS RES. 15, 2891 (1987) incorporated by reference).

These surface-attached or adsorbed molecules are best added to the microparticles after the fluorescent dyes have been incorporated. Where a variety of target complements are attached to a single microparticle, the number of different target complements that can be effectively attached will depend on the size and type of microparticles and the characteristics of the respective target complements. Although hundreds of thousands of individual target complement molecules are often attached to a single microparticle (e.g. avidin-labeled microparticles routinely contain in excess of 1.5 million biotin binding sites), typically, the number of different types of target complements on a single microparticle will be less than 1000, more typically less than 100, even more typically less than 10. The target complement(s), which optionally coats the microparticle surface partially or completely, is present in sufficient amount that the microparticle selectively attaches to and forms a complex with the target material or materials.

It is a particular advantage of the subject microparticles that several microparticle-labeled probes can be prepared where all the probes have the same excitation peak of the initial donor dye but each probe has a different emission peak detectably distinct from the emission peaks of the other probes. As a result, these microparticles are particularly suited for the simultaneous detection of multiple different target complements. Unlike radioactive methods, chemiluminescent labels or direct fluorophore conjugates, the subject microparticles can be made in a wide range of spectrally distinct colors that are simultaneously excitable with inexpensive, easily available equipment, such as hand-held uv lamps, and whose emission can be easily detected and distinguished by eye. Adding instrumental means for exciting and isolating the fluorescence signal tremendously expands the number of detectably different labels that are possible.

Using the method of the instant invention, as many different labels can be made as can be resolved by appropriate choice of wavelength-selective elements such as filters, monochromators, or photodiode arrays, or other methods for discriminating fluorescent signals such as by pulse or phase-modulation techniques; each different label allowing the detection of a different analyte. Thus, having "X" detectably different microparticles would allow X different microparticle-labeled probes to be combined with a single sample mixture, resulting in the detection of X independent target materials in that mixture. For example, the presence of mycoplasma, viruses or plasmid species in the cytoplasm can be visibly distinguished from chromosomal or plasmid borne genes in the nucleus of a single cell (or in sections of a developing embryo), using in situ hybridization; or the presence of RNA or DNA molecules corresponding to as many as X different genes can be simultaneously assayed in Northern, Southern or spot blots or through solution hybridization; or the location of as many as X different genes could be determined with respect to one another on eucaryotic chromosomes on chromosome squashes or spreads, using in situ hybridization.

Alternatively, multicolor labeling is accomplished using combinatorial mixtures of microparticle-labled probes, similar to the technique described by Nederlof, et al. using fluorescent dyes (CYTOMETRY 11, 126 (1990)). There is a different mixture for each target material but the number of different microparticles used in each mixture is less than the total number of mixtures (Example 13; Table 5). The different microparticles are mixed such that any given mixture has a characteristic percentage (from 0% to 100%) of each of the different microparticles. The characteristic percentage of each of the different microparticles give the mixture a detectably distinct set of spectral properties (FIGS. 4–6). The microparticle-labled probes in a given mixture contain the same target complement. Typically, combinatorial mixtures of microspheres with the same excitation wavelength and different maximal emissions are used, although mixtures with the same maximal emissions and different maximal absorptions can also be distinguished.

Formation of microparticle-labeled probes for such multicolor detection can be mediated in a variety of ways. These include, e.g. for nucleic acids, a) direct nucleic acid-microparticle conjugates (with or without linker molecules), b) conjugation through the use of biotinylated nucleic acids and avidin labeled microparticles, or biotinylated nucleic acids, streptavidin, and biotinylated microparticles, c) digoxigenin labeled nucleic acids and antibodies to digoxigenin coupled to microparticles, d) nucleic acids labeled with other antigenic substances, such as fluorescein, or dinitrophenyl groups, detected with antibodies coupled to microparticles, or e) nucleic acids labeled with any antigenic substance, followed by reaction with the appropriate antibody, followed by detection with protein A coupled microparticles. Similar techniques can be used for other members of specfic binding pairs, e.g. proteins, drugs, etc., where appropriate complementary binding pairs are available. Typically, such techniques are used with antibodies, for instance where one antibody recognizes all T cells and a second antibody recognizes only a subset of T cells. These various detection techniques can also be combined to get multicolor detection that is multiply mediated.

For use in combination with fluorescent microparticles with a contollable Stokes shift, additional fluorescent detection reagents, including conventional fluorescent microparticles, that are selective for a wide range of target materials are commericially available (e.g. Haugland, MOLECULAR PROBES HANDBOOK OF FLUORESCENT PROBES AND RESEARCH REAGENTS (1992–1994)). Fluorescent microparticles may be purchased or prepared from any fluorescent dyes described above without utilization of their energy transfer characteristics. Such dyes are selected for their spectral properties in conjunction with polymeric microparticles and applied to or incorporated into the microparticles according to any methods generally known in the art, including methods described herein. Such fluorescent microparticles are likewise labeled with probes that are complementary to target materials, according to known methods, including those described above. Alternatively or additionally, reagents that are useful in combination with fluorescent microparticle-labeled probes include, for example, nucleic acid stains, enzyme substrates, organellar probes, membrane probes, receptor probes, colloidal gold particles, and fluorescent antibodies.

Labeling of Target Materials

The subject fluorescent microparticles are ideal reagents for the detection of a variety of target materials, including nucleic acids (e.g. RNA and DNA), proteins and carbohydrates. The microparticles are relatively safe and non-toxic in comparison to radioactivity, which is the standard reagent used for such detection, yet the limits of detection with these microparticles rival those of radioactivity. They are chemically more stable than fluorophores currently in use and are easier to use than the reagents that require secondary detection through coupled enzymatic activity or antibodies. In addition, they can be coupled to antibodies for secondary detection, if signal enhancement is needed. Finally, because the novel microparticles can be tailored to emit at a variety of wavelengths, and have significant intensity at any of several selectable wavelengths, they can readily be used to do simultaneous or sequential multicolor detection of different target materials, such as differernt nucleic acid species or different antigens.

Although the use of labeled microparticles to detect and identify target materials such as nucleic acids is known (see references above), the subject microparticles have numerous advantages over others that have been described. Because of the long effective Stokes shift that can be achieved, it is possible to use the subject microparticles for applications where the intrinsic autofluorescence of the sample (as is present in algae or other plant cells, for example) or the presence of pigments (e.g. heme or xanthene) normally interferes with the signal. Furthermore, the subject microparticles can be prepared with modified surfaces that reduce non-specific binding. This characteristic enormously increases signal-to-background for any hybridization technique, allowing the use of standard hybridization filters as opposed to published protocols using labeled microparticles, which require the use of a membrane with an unusually modified surface. Furthermore, the subject microparticles are significantly brighter than those currently available, resulting in detection limits up to orders-of-magnitude lower than is possible with any other labeled microparticles.

The microparticle-labeled probes described above, whether for single or multicolor detection systems, are combined with a sample thought to contain target materials. Typically the sample is incubated with an aqueous suspension of the microparticle-labeled probes. Where a single color detection system is used, the aqueous suspension contains substantially identical microparticle-labeled probes. Where a multicolor detection system is used, the aqueous suspension contains a number of detectably different microparticle-labeled probes. In each case, the microparticle-labeled probe is specific for a particular target or combination of targets.

Prior to combination with the microparticle-labeled probes, the sample is prepared in a way that makes the target materials in the sample accessible to the probes. The target materials may require purification or separation prior to labeling or detection. For example, the sample may contain purified nucleic acids, proteins, or carbohydrates, either in mixtures or individual nucleic acid, protein, or carbohydrate species; the sample may contain nucleic acids, proteins, or carbohydrates in lysed cells along with other cellular components; or the sample may contain nucleic acids, proteins, or carbohydrates in substantially whole, permeabilized cells. Preparation of the sample will depend on the way the target materials are contained in the sample.

When the sample contains purified target materials, the purified target materials may still be mixtures of different materials. For example, purified protein or nucleic acid mixtures may contain several different proteins or nucleic acids. Alternatively, the purified target materials may be electrophoresed on agarose or polyacrylamide gels to provide individual species of target materials. Preparation of a sample containing purified nucleic acids or proteins generally includes denaturation and neutralization. DNA may be denatured by incubation with base (such as sodium hydroxide) or heat. RNA is also denatured by heating (for spot blots) or by electrophoresing in the presence of denaturants such as urea, glyoxal, or formaldehyde, rather than through exposure to base (for Northern blots). Proteins are denatured by heating in combination with incubation or electrophoresis in the presence of detergents such as sodium dodecylsulfate. The nucleic acids are then neutralized by the addition of an acid (e.g. hydrochloric acid), chilling, or addition of buffer (e.g. Tris, phosphate or citrate buffer), as appropriate.

Typically, the preparation of a sample containing purified target materials further comprises immobilization of the target materials on a solid or semi-solid support. Purified nucleic acids are generally spotted onto filter membranes such as nitrocellulose filters or nylon membranes in the presence of appropriate salts (such as sodium chloride or ammonium acetate) for DNA spot blots. Alternatively, the purified nucleic acids are transferred to nitrocellulose filters by capillary blotting or electroblotting under appropriate buffer conditions (for Northern or Southern blots). To permanently bind nucleic acids to the filter membranes, standard crosslinking techniques are used (for example, nitrocellulose filters are baked at 80° C. in vacuo; nylon membranes are subjected to illumination with 360 nm light). The filter membranes are then incubated with solutions designed to prevent non-specific binding of the nucleic acid probe (such as BSA, casein hydrolysate, single-stranded nucleic acids from a species not related to the probe, etc.) and hybridized to probes in a similar solution. Purified proteins are generally spotted onto nitrocellulose or nylon filter membranes after heat and/or detergent denaturation. Alternatively, the purified proteins are transferred to filter membranes by capillary blotting or electroblotting under appropriate buffer conditions (for Western blots). Non-specifically bound probe is washed from the filters with a solution such as saline citrate or phosphate buffer. Filters are blocked with agents to prevent non-specific adherence of microparticles (such as detergent). Finally, samples are probed with labeled microparticles. Non-specifically bound microparticles are typically removed by washing with more blocking buffer.

When the sample contains cellular nucleic acids (such as chromosomal or plasmid borne genes within cells, RNA or DNA viruses or mycoplasma infecting cells, or intracellular RNA) or proteins, preparation of the sample involves lysing or permeabilizing the cell, in addition to the denaturation and neutralization already described. Cells are lysed by exposure to agents such as detergent (for example sodium dodecyl sulfate, Tween, sarkosyl or Triton), lysozyme, base (for example sodium, lithium or potassium hydroxide), chloroform, or heat. Cells are permeabilized by conventional methods, such as by formaldehyde in buffer.

As with samples containing purified target materials, preparation of the sample containing cellular target materials typically further comprises immobilization of the target materials on a solid or semi-solid support. In lysed cells, cells in suspension are spotted onto or filtered through nitrocellulose or nylon membranes, or colonies of cells are grown directly on membranes that are in contact with appropriate growth media, and the cellular components, such as nucleic acids, are permanently bound to filters as described above. Permeabilized cells are typically fixed on situ microscope slides with known techniques used for in situ hybridization and hybridization to chromosome "squashes" and "spreads," (e.g. with a reagent such as formaldehyde in a buffered solution). Slides are then treated with a solution (such as triethanolamine and acetic anhydride) to block non-specific binding of the microparticles and treated with a buffering solution (such as Tris/glycine, phosphate buffered saline, or saline citrate). Finally, samples are dehydrated to prepare them for microscopy (with reagents such as a graded series of ethanol dilutions) and dried. Prehybridization and hybridization solutions, blocking, probing and washing on the solid support are essentially as described above.

Following the labeling of the sample with the microparticle-labeled probes, unbound probes are optionally removed from the sample by conventional methods such as washing. For detection of the target materials, the sample is illuminated with means for exciting fluorescence in the microparticle-labeled probes. Typically a source of excitation energy emitting within the range of the excitation peak of the initial donor dye of the microparticle-labeled probes is used. Fluorescence resulting from the illuminated microparticle-labled probes that have formed a complex with the target materials can be used to detect the presence, location, or quantity of target materials.

Fluorescence from the microparticle-labeled probes can be visualized with a variety of imaging techniques, including ordinary light or fluorescence microscopy and laser scanning confocal microscopy. Three-dimensional imaging resolution techniques in confocal microscopy utilize knowledge of the microscope's point spread function (image of a point source) to place out-of-focus light in its proper perspective. Mutiple labeled target materials are optionally resolved spatially, chronologically, by size, or using detectably different spectral characteristics (including excitation and emission maxima, fluorescence intensity, or combinations thereof). Typically, multiple labeled target materials are resolved using different microparticle-labeled probes with distinct spectral characteristics for each target material. Alternatively, the microparticles are the same but the samples are labeled and viewed sequentially or spatially separated. If there is no need or desire to resolve multiple targets, as in wide scale screening (e.g. pan-viral or bacterial contamination screening), microparticles containing multiple target complements need not be separately applied to samples.

The following illustrations describe the practice of the invention and are by way of example and not by way of limitation.

EXAMPLE 1

Preparation of 4,4-Difluoro-5,7-diphenyl-3-(pyrrol-2-yl)-4-bora-3a,4a-diaza-s-indacene (Compound 6)

To a solution of 90 mg (0.36 mmol) of 3,5-diphenylpyrrole-2-carboxaldehyde and 50 mg (0.37 mmol) of 2,2'-bipyrrole in 15 mL of dichloromethane is added 40 µL (0.45 mmol) of phosphorus oxychloride. The reaction mixture is stirred at room temperature for 12 hours and is added 225 µL (1.62 mmol) of N,N-diisopropylethylamine, followed by addition of 200 µL (1.62 mmol) of boron trifluoride etherate. After the whole mixture is stirred at room temperature for 2 hours, it is washed with two 20 mL portions of water. The organic layer is separated, dried over anhydrous sodium sulfate and concentrated under reduced pressure to give a dark purple-blue solid. The crude product is purified by chromatography on silica gel with 30% chloroform in hexane as eluant to give 49 mg (33%) of a dark purple-blue solid.

2,2'-Bipyrrole is prepared as described in H. Rapoport et al., J. AM. CHEM. SOC. 114, 2178 (1962). 3,5-Diphenyl-2-pyrrolecarboxaldehyde is prepared from 2,4-diphenylpyrrole by the Vilsmeyer Haak formylation, according to R. M. Silverstein et al., ORG. SYNTH. COLL. Vol. IV, p. 831.

Compounds 1 and 2 are prepared by the reaction of pyrrole-2-carboxaldehyde and 3,5-dimethylpyrrole-2-carboxaldehyde, respectively with 2,4-dimethylpyrrole as described in EXAMPLE 1. Compounds 3 and 4 are prepared by the reaction of 2,4-dimethylpyrrole and 2,4-diphenylpyrrole, respectively, with 3,5-diphenylpyrrole-2-carboxaldehyde as described in EXAMPLE 1.

EXAMPLE 2

Preparation of 4,4-Difluoro-1,3,5,7-tetraphenyl-4-bora-3a,4a,8-triaza-s-indacene (Compound 5)

A mixture of 85 mg (0.40 mmol) of 2,4-diphenylpyrrole and 100 mg (0.40 mmol) of 2-nitroso-3,5-diphenylpyrrole in 5 mL of glacial acetic acid is heated under reflux for 3 hours. After the reaction mixture is cooled to room temperature, it is poured into 20 mL of ether. The resulting precipitate is collected by filtration, washed with ether and dried to give a 89 mg of a blue solid. This solid is dissolved on 10 mL of dichloromethane and are added 100 µL (0.57 mmol) of N,N-diisopropylethylamine and 70 µL (0.51 mmol) of boron trifluoride etherate. After the reaction mixture is stirred at room temperature for 2 hours, it is worked-up and purified in a similar way as described in EXAMPLE 1 to give a 80 mg (40%) of Compound 5 as a dark blue solid.

EXAMPLE 3

Preparation of Novel Microparticles Using Two Polyazaindacene Dyes

To a vigorously stirred 200 mL suspension 0.093 micrometer carboxylate-modified latex (Interfacial Dynamics Corp., Portland, Oreg.; 3.05% solids in 50% v/v distilled water/methanol) is added a solution of 50 mg of Compound 1 and 17 mg of Compound 3 dissolved in a homogeneous mixture of 9 mL of dichloromethane and 16 mL of absolute ethanol. The addition of the dye is carried out by means of a syringe pump fitted with a Teflon delivery tube (0.038 in i.d.) and the dye solution is delivered at a flow rate of 6 mL/hr. After addition is complete, the suspension is filtered through loosely packed glass wool to remove any debris and then partially evaporated at room temperature on a rotary evaporator to remove the dichloromethane and alcohols. The aqueous suspension of dyed latex is then filtered again through glass wool to remove any additional debris and dialyzed (25 mm tubing, MW cutoff 12,000–14,000) to remove any residual dye. The dialysis is carried out until no more free dye is removed from the particles as detected by fluorimetric analysis of the dialysate. The fluorescent latex suspension is removed from dialysis and filtered again through glass wool to remove any remaining aggregates and other debris. The suspension is then sonicated in a bath sonicator for 10 minutes to ensure monodispersity. Visual analysis of a dilute aqueous suspension of the product by fluorescence microscopy using standard rhodamine filters shows uniformly dyed particles that are highly monodisperse. Spectral analysis of the product, exciting at 480 nm shows a single emission peak centered at 557 nm.

EXAMPLE 4

Preparation of Novel Microparticles Using Three Polyazaindacene Dyes

To a vigorously stirred 200 mL suspension 0.030 micrometer carboxylate-modified latex (Interfacial Dynamics Corp., Portland, Oreg.; 3.67% solids in 50% v/v distilled water/methanol) is added a solution of 50 mg of Compound 1, 17 mg of Compound 3 and 22 mg of Compound 4 dissolved in a homogeneous mixture of 7.5 mL of dichloromethane and 17.5 mL of absolute ethanol. The addition of the dye and purification of the product is carried out as described in EXAMPLE 3. Visual analysis of a dilute aqueous suspension of the product by fluorescence microscopy using standard Texas Red compatible filters shows uniformly dyed particles that are highly monodisperse. Spectral analysis of the product, exciting at 480 nm shows a single emission peak centered at 605 nm.

EXAMPLE 5

Preparation of Novel Microparticles Using Two Coumarin Dyes

To a vigorously stirred 200 mL suspension 0.282 micrometer carboxylate-modified latex (Interfacial Dynamics Corp., Portland, Oreg.; 2.75% solids in 50% v/v distilled water/methanol) is added a solution of 30 mg of Coumarin 138 (Eastman Kodak, Rochester, N.Y.) and 30 mg of Coumarin 314 (Eastman Kodak) dissolved in a homogeneous mixture of 7.5 mL of dichloromethane and 17.5 mL of absolute ethanol. The addition of the dye and purification of the product is carried out as described in EXAMPLE 3. Visual analysis of a dilute aqueous suspension of the product by fluorescence microscopy using standard AMCA excitation and emission filters shows uniformly dyed particles that are highly monodisperse. Spectral analysis of the product, exciting at 360 nm shows an emission peak centered at 410 nm and an emission peak centered at 460 nm. The integrated ratio of the 460 nm peak (from coumarin 314) to the 410 peak (from coumarin 138) is 92:8, indicating efficient transfer of emission energy from coumarin 138 to coumarin 314.

EXAMPLE 6

Preparation of Novel Microparticles Using One Polyolefin Dye and One Polyazaindacene Dye To a vigorously stirred 200 mL suspension 0.977 micrometer carboxylate-modified latex (Interfacial Dynamics Corp., Portland, Oreg.; 2.10% solids in 50% v/v distilled water/methanol) is added a solution of 50 mg of diphenylhexatriene (DPH) and 10 mg of Compound 1 dissolved in a homogeneous mixture of 9 mL of dichloromethane and 16 mL of absolute ethanol. The addition of the dye and purification of the product is carried out as described in EXAMPLE 3. Visual analysis of a dilute aqueous suspension of the product by fluorescence microscopy using standard fluorescein filters shows uniformly dyed particles that are highly monodisperse. Spectral analysis of the product, exciting at 365 nm shows an emission peak centered at 430 nm and a second emission peak centered at 512 nm. The integrated ratio of the 430 nm peak (from DPH) to the 512 peak (from Compound 1) is 74:26, indicating efficient transfer of emission energy from DPH to Compound 1. As a further confirmation of the effectiveness of the energy transfer, 0.093 micron latex particles are prepared as described above with 10 mg of Compound 1 only. When these latex particles are excited at 365 nm under the same conditions as the particles containing both DPH and Compound 1, the integrated area of the 512 nm peak is less than 10% of that obtained in the two dye system.

EXAMPLE 7

Preparation of Novel Microparticles Using One Coumarin Dye and One Polyazaindacene Dye To a vigorously stirred 200 mL suspension 0.282 micrometer carboxylate-modified latex (Interfacial Dynamics Corp., Portland, Oreg.; 2.10% solids in 50% v/v distilled water/methanol) is added a solution of 50 mg of coumarin 6 and 50 mg of Compound 1 dissolved in a homogeneous mixture of 9 mL of dichloromethane and 16 mL of absolute ethanol. The addition of the dye and purification of the product is carried out as described in EXAMPLE 3. Visual analysis of a dilute aqueous suspension of the product by fluorescence microscopy using standard fluorescein excitation and emission filters shows uniformly dyed particles that are highly monodisperse. Spectral analysis of the product, exciting at 430 nm shows the major emission peak to be centered at 512 nm. There is a smaller emission peak centered at 520 nm from the coumarin 6, indicating substantial, but not complete energy transfer.

EXAMPLE 8

Preparation of Avidin-Labeled Novel Microparticles Using Two Polyazaindacene Dyes To a 15 mL glass centrifuge tube is added 2 mL 50 mM MES (2-[N-morpholino]ethane sulfonic acid) buffer, pH 6.0; 4 mg of avidin (allow to completely dissolve); and 5 mL of a 2% aqueous suspension of the latex microspheres prepared in EXAMPLE 6. The mixture is agitated and incubated at room temperature for 15 minutes. Then 40 mg of 1-ethyl-3-(dimethylaminopropyl)-carbodiimide (EDAC) is added and the tube is agitated to mix the contents. The pH is adjusted to 6.5±0.2 with dilute NaOH and the reaction mixture is incubated with gentle mixing on a rocker or orbital shaker for 2 hours at room temperature. The avidin-labeled latex microspheres are separated from unbound avidin by centrifugation at 2,000 RPM for 20 minutes. The supernatant is decanted and the avidin-labeled latex pellet is re-suspended in PBS, pH 7.4 and washed 3 times by centrifugation/decantation. The avidin-labeled latex is suspended in a final volume of 5 mL of PBS, pH 7.4.

Biotinylated latex microspheres are prepared according to the procedure of EXAMPLE 8 using BSA conjugated to 6-((6-((biotinoyl)amino)hexanoyl)amino)hexanoic acid in place of avidin.

EXAMPLE 9

Detection of M13 DNA Spotted onto Nitrocellulose Filters

Nitrocellulose filters (BA 85, 0.45 micron pores, Schleicher and Schuell, Keene, N.H.) are pretreated by incubation with water, then 20× SSC (175 g NaCl, 88 g sodium citrate, pH 7.0, per liter) and air dried. M13 single-stranded DNA is diluted serially in T.E. (10 mM Tris-Cl, pH 7.8, 1 mM EDTA) in microfuge tubes and spotted onto these filters. Filters are air dried, then baked 1 hour, 80° C., in a vacuum oven. Prehybridization is done by incubation in 6× SSC (52.5 g NaCl, 26.4 g sodium citrate, pH 7.0 per liter), 0.5% sodium dodecyl sulfate (SDS), 5× Denhardt's (0.1% Ficoll, 0.1% polyvinylpyrrolidone, 0.1% bovine serum albumin (BSA)) and 100 micrograms/mL single stranded DNA, 1 hour, at 60° C. Hybridization is done in the same solution with the addition of 30 ng/mL M13 biotinylated oligonucleotide probe at the same temperature for 3 hours. The filters are washed by incubation in 6× SSC, 0.1% SDS for 20 minutes at room temperature and then for 5 minutes at 60° C. Filters are then blocked by incubation in 100 mM Tris, 150 mM NaCl, pH 7.8, 0.05% non-fat dried milk, 0.5% Tween-20 for 1 hour. Labeling is done by incubation at room temperature for 1 hour in the same solution containing a 1:1000 dilution of the microparticles prepared in EXAMPLE 8 (2% solids), which are avidin conjugated and fluorescently labeled. Finally, non-specifically adsorbed microparticles are removed by washing filters in the same solution without non-fat dried milk, for 10 minutes, at room temperature. Spots are visualized by illumination with 360 nm light.

EXAMPLE 10

Detection of Gene Specific mRNA in Lysed Tissue Culture Cells.

A suspension of $1 \times 10^4$ CREBAG (positive for the lacZ gene) or NIH3T3 cells (negative for the lacZ gene) is spotted onto nitrocellulose filters (BA85, 0.45 micron pores, Schleicher and Schuell, Keene, N.H.). The cells are lysed by incubation with 100 mM NaCl, 10 mM Tris-Cl, pH 7.8, 25 mM EDTA and 0.5% sodium dodecyl sulfate (SDS). The DNA is denatured by incubation with 1.5M NaCl, 0.5M NaOH for 5 minutes, then neutralized by incubation for 5 minutes with 100 mM Tris-Cl, pH 7.8, 150 mM NaCl. The filters are baked 1 hour at 80° C. in a vacuum oven. Filters are then prehybridized by incubation with 6× SSC, 5× Denhardt's, 0.5% SDS, and 100 micrograms/mL salmon sperm DNA for 1 hour at 60° C. Hybridization is done in the same solution, with the addition of 30 ng/mL biotinylated M13 oligonucleotide probe (which hybridizes to the lacZ gene), incubated 1 hour at 60° C. Filters are washed with 6× SSC containing 0.1% SDS for 20 minutes at room temperature, then in the same solution for 5 minutes at 60° C. The filters are then blocked to prevent non-specific binding of the microparticles by incubation with 100 mM Tris-Cl, pH 7.8, 150 mM NaCl, 0.5% Tween-20 and 3% w/v bovine serum albumin (BSA) for 1 hour at room temperature. The microparticles prepared in EXAMPLE 8 (biotinylated, fluorescently labelled microparticles, 2% solids) are added in a final dilution of 1:1000 to the blocking buffer and incubated with the filters for 30 minutes at room temperature. Filters are then washed with 100 mM Tris, pH 7.8, 150 mM NaCl for 30 minutes at room temperature and the signal visualized by irradiation with a hand-held UV lamp (UVP, Inc., San Gabriel, Calif.) with a broad-bandwidth filter centered at about 360 nm. The CREBAG cells show clearly visible yellow-green fluorescence while the NIH3T3 cells do not.

EXAMPLE 11

Detection of Gene Specific mRNA by In Situ Hybridization.

CREBAG (lacZ positive) or NIH3T3 (lacZ negative) cells growing on a microscope slide are permeabilized and fixed by incubation for 15 minutes in 3.7% formaldehyde in PBS (8 g sodium chloride, 0.2 g KCl, 1.44 g $Na_2HPO_4$, 0.24 g $KH_2PO_4$, pH 7.4, per liter). Slides are rinsed twice in 2× SSC (17.5 g sodium chloride, 8.8 g sodium citrate, pH 7.0, per liter) for 1 minute, then incubated for 10 minutes 0.1M triethanolamine/0.25% acetic anhydride. Cells are then equilibrated for 1 minute in 2× SSC, for 1 minute in PBS, and for 30 minutes in 0.1M Tris/glycine buffer, pH 7.0. Slides are rinsed twice in 2× SSC, then dehydrated in 70% and 95% ethanol then air dried. Prehybridization is done by incubation of each slide with 300 microliters of a solution containing 50% formamide, 5× Denhardt's (0.1% Ficoll, 0.1% polyvinylpyrrolidone, 0.1% bovine serum albumin (BSA)), 6× SSPE (1.08M sodium chloride, 60M $NaH_2PO_4$, pH 7.4, 6 mM EDTA), 250 micrograms/mL *E. coli* tRNA, 500 micrograms/mL calf thymus DNA for 1 hour at room temperature. Hybridization is done using the same volume of the same solution with the addition of 2 micrograms/mL biotinylated oligonucleotide probe and incubated overnight at 42° C. Filters are then washed several times with 2× SSC, blocked by incubation with PBS containing 3% BSA and 0.1% Tween 20 and incubated with a 1:1000 dilution of microparticles as prepared in EXAMPLE 8 above (avidin labeled fluorescent microparticles, 2% solids) for 30 minutes at room temperature. Slides are washed briefly with PBS and visualized. Viewed with a microscope with a UV light source, the CREBAG cells show easily detectable green ;fluorescence while the NIH3T3 cells do not.

EXAMPLE 12

Detection of mRNA Molecules Using Northern Blotting.

Microparticles are directly conjugated to oligonucleotide probes directed against the zebrafish engrailed, inverted and HOX (homeobox) genes, as well as the CAT (chloramphenicol acetyl transferase) gene, using any one of the methods described in the literature. The oligonucleotide probes are each conjugated to differently labeled 0.1 micron microparticles: engrailed to yellow green (emission 512 nm, latex incorporating Compound 1), inverted to orange (emission 557 nm, latex incorporating Compounds 1 & 3 as in EXAMPLE 3), HOX to red (emission 605 nm, latex incorporating Compounds 1, 3, & 4, as in EXAMPLE 4) and CAT to crimson (emission 650 nm, latex incorporating Compounds 1, 3, 4 & 6). Total cellular RNA is prepared from zebrafish embryos at several different stages of development. RNA is prepared by cellular disruption (using a baked glass homogenizer, in the presence of homogenization buffer, consisting of 50 mM NaCl, 50 mM Tris-Cl, pH 7.5, 5 mM EDTA, 0.5% sodium dodecyl sulfate (SDS), and 200 micrograms/mL proteinase K) and incubated for 1 hour at 37° C. to digest proteins. The homogenate is extracted with an equal volume of phenol:chloroform, 1:1, and the aqueous phase reextracted twice more with the same solution. The nucleic acids are precipitated by the addition of 0.1 volume of 3M sodium acetate (pH 5.2) and 2.5 volumes of ice cold ethanol, incubated 2 hours on ice. Nucleic acids are pelletted by centrifugation at 5000×g for 15 minutes at 4° C., the supernatant is discarded, and the pellet allowed to air dry. Total nucleic acids (consisting mainly of RNA) are dissolved in sterile water.

10 micrograms of RNA per lane is glyoxylated using standard methods and electrophoresed on an agarose gel (1% agarose in 0.01M sodium phosphate, pH 7.9). The RNA is subjected to capillary transfer in 20× SSPE (174 g NaCl, 27.6 g $NaH_2PO_4.H_2O$ and 7.4 g EDTA, pH 7.4, per liter) to a nitrocellulose filter membrane (BA85, 0.45 micron pores, Schleicher and Schuell, Keene, N.H.) that is pre-equilibrated in 2× SSC (17.5 g NaCl, 8.8 sodium citrate, pH 7.0 per liter). The nitrocellulose filter membrane is baked for 1 hour at 80° C., in a vacuum oven to permanently bind nucleic acids. The blot is then prehybridized by incubation with 6× SSC (52.5 g NaCl, 26.4 g sodium citrate, pH 7.0, per liter), 0.5% SDS, 5× Denhardt's (0.1% Ficoll, 0.1% polyvinylpyrrolidone, 0.1% bovine serum albumin (BSA)), 0.05% non-fat dried milk, 0.5% Tween-20 and 100 micrograms/mL single stranded DNA for 1 hour at 60° C. The filters are then hybridized in the same solution, with the addition of 30 ng/mL of each microparticle-conjugated oligonucleotide probe, at the same temperature, for 3 hours. The filters are then washed with 6× SSC, 0.1% SDS for 20 minutes at room temperature and then for 5 minutes at 60° C. to remove non-specifically adsorbed probe. Bands corresponding to individual RNA species are visualized by illumination with a hand-held uv light source (UVP, Inc., San Gabriel, Calif.) with a broad bandwidth filter centered at about 360 nm. Each RNA species shows a distinct color, showing that RNA corresponding to the CAT gene is produced at all stages during development, while RNAs corresponding to engrailed, HOX and invertedgenes are only present at defined periods during development.

EXAMPLE 13

Combinatorial Mixtures

Latex samples are prepared by mixing 1 μL aliquots, taken from a stock solution that is 2% solids, of the following combinations of 0.1 μm carboxylate-modified fluorescent microspheres (Table 5), diluted into 1 mL of distilled water. Yellow fluorescent microspheres have a series of dyes that give an excitation maximum at about 488 nm and emission maximum at about 560 nm; orange fluorescent microspheres have a series of dyes that give an excitation maximum at about 488 nm and an emission maximum at about 645 nm; red fluorescent microspheres have a series of dyes that give an excitation maximum at about 488 nm and an emission maximum at about 720 nm. All of the mixtures are excited at 480 nm. Fluorescence emission is measured in a standard fluorometer, at 560 nm for the yellow, 645 nm for the orange and 720 nm for the red microspheres (FIGS. 4–6), mixtures result in distinct emissions at each wavelength. Table 5 shows that the percentages of each distinct microsphere in the mixture is a direct indicator of the fluorescence emission intensity of the microsphere mixture at each wavelength, within a normal experimental margin of error.

TABLE 5

COMBINATORIAL MIXTURES

| Mixture # | Latex Microsphere Percentages | | | Actual Fluorescence Emission | | |
|---|---|---|---|---|---|---|
| | yellow | orange | red | 560 nm | 645 nm | 720 nm |
| 1 | 100% | — | — | 100% | — | — |
| 2 | 75% | 25% | — | 72% | 28% | — |
| 3 | 50% | 50% | — | 47% | 54% | — |
| 4 | 25% | 75% | — | 23% | 78% | — |
| 5 | — | 100% | — | — | 100% | — |
| 6 | 100% | — | — | 100% | — | — |
| 7 | 75% | — | 25% | 74% | — | 27% |
| 8 | 50% | — | 50% | 49% | — | 53% |
| 9 | 25% | — | 75% | 25% | — | 77% |
| 10 | — | — | 100% | — | — | 100% |
| 11 | — | 100% | — | — | 100% | — |
| 12 | — | 75% | 25% | — | 73% | 26% |
| 13 | — | 50% | 50% | — | 50% | 53% |
| 14 | — | 25% | 75% | — | 25% | 77% |
| 15 | — | — | 100% | — | — | 100% |

EXAMPLE 14

Western Blot Detection

Bovine heart cytochrome c oxidase (COX), which contains 13 different subunits, is serially diluted into protein gel loading buffer and electrophoresed on a 12% sodium dodecyl sulfate (SDS) protein gel using standard procedures. After electrophoresis, the proteins are electrophoretically transfered to 0.2 μm pore size nylon membrane, using standard procedures. Lanes contain from 10 pg to 4 ng total COX protein. The membrane is then blocked by incubation with BLOTTO (Pierce). The membrane is then incubated with a mixture of 0.28 μm fluorescent carboxylate-modified latex microspheres (0.2% solids final concentration) in phosphate buffered saline (PBS). Each microsphere preparation in the mixture has a distinct fluorescence emission and has bound to its surface a distinct monoclonal antibody directed against a different COX subunit. For example, yellow-green microspheres are coated with monoclonal antibodies directed against subunit IV, orange microspheres are coated with antibodies directed against subunit III, red microspheres are coated with antibodies directed against subunit II, etc. The membrane is washed with PBS and fluorescent bands are visualized using ultraviolet light with excitation ranging from 245 nm to about 365 nm, on a standard trans or epi-illuminator. Fluorescent bands are photographed using Polaroid 667 black and white print film and a Kodak yellow Wratten filter, or using Ektachrome 400 ASA color slide film and a 410 longpass filter. All lanes show some detectable fluorescence, in at least some bands, upon appropriate film exposures. Each band shows a distinct, different color emission, corresponding to the protein subunit present in that band.

EXAMPLE 15

Cell Surface Receptor Detection

Detection of Concanavalin A (Con A) receptors on human lymphocytes in suspension. Human lymphocytes are grown in suspension, fixed with 3.7% formaldehyde in 10 mM sodium phosphate, 0.85% NaCl, pH 7.2 (PBS) and then incubated with biotinylated Con A. Cells are pelleted by centrifugation for 5 minutes at 2000 rpm in a benchtop centrifuge onto microtiter plates and then washed with PBS. A solution containing 3 µl of 14 nm yellow-green streptavidin-modified carboxylate-modified latex fluorescent microspheres (2% solids) diluted into 40 ml of PBS, 0.2% Tween-20, 3% bovine serum albumin (BSA) is incubated with the cells. Cells are once again pelleted in microtiter plates and washed briefly with PBS containing 0.2% Tween 20 and resuspended in the same solution. An aliquot of labeled cells is removed from each well and applied to a coverslip. Labeled cells are visualized in the fluorescence microscope using a standard fluorescein filter set.

Detection of ConA receptors on fixed NIH3T3 mouse fibroblasts. Adherent fibroblasts are grown on coverslips and treated as described above, except that instead of pelleting cells onto microtiter plates, coverslips are simply incubated in the indicated solutions and visualized directly as above.

EXAMPLE 16

Chromosome In Situ Hybridization

Detection of centromeres on human chromosomes by in situ hybridization. Human chromosome spreads are prepared on microscope slides from peripheral blood according to standard procedures. Spreads contain both interphase nuclei and metaphase chromosomes. Biotinylated probes directed against human centromeres (obtained from ONCOR) are hybridized with the chromosome preparations. Excess probe DNA is removed by washing slides briefly with 0.3M NaCl, 30 mM sodium citrate, pH 7.0 (2× SSC). Samples are then incubated in a solution containing PBS, 0.2% Tween 20 and 3% BSA to block non-specific binding of the microspheres. Centromeres are then labeled by incubation of the slides in a 40 mL solution of PBS, 0.2% BSA containing 3 µL 14 micron yellow-green fluorescent streptavidin-coated carboxylate-modified microspheres (2% solids) and 1 µg/mL propidium iodide as a counterstain. Slides are then washed and visualized in the fluorescence microscope using a fluorescein filter set. Centromeres are easily visible as brightly labeled fluorescent green signals in the appropriate regions of red fluorescent chromosomes or as distinct green fluorescent spots on red interphase nuclei.

EXAMPLE 17

Quantitation of Nucleic Acids

Quantitation of single-stranded M13 bacteriophage DNA using a biotinylated oligonucleotide probe and streptavidin-coated yellow-green fluorescent microspheres. A dilution series of single-stranded M13 DNA (diluted into a 500 ng/µl solution of denatured herring sperm DNA in 10 mM Tris, 1 mM EDTA, pH 8.0 (T.E.)), consisting of amounts such as 50 ng, 25 ng, 12.5 ng, 6.3 ng, 3.2 ng, 1.6 ng, 0.8 ng, 0.4 ng and 0 DNA per 1 µL spot, is spotted onto a nitrocellulose filter membrane that has been pretreated with 3M NaCl, 0.3M sodium citrate, pH 7.0 (20× SSC) and air-dried. Samples containing unknown amounts of M13 DNA are prepared according to standard procedures from infected bacterial cells. Fresh M13 plaques are picked using sterile glass capillaries, innoculated into 2 mL of bacterial growth media in sterile glass culture tubes, and allowed to propagate at 37° C., shaking, for 4.5 hours. Bacterial cells and debris are pelleted by centrifugation for 3 minutes at room temperature at 5000 rpm in a benchtop microcentrifuge. 1.2 mL of the cleared supernatant is transferred to a fresh microfuge tube. A solution containing 20% polyethylene glycol in 2.5M NaCl is added to the supernatant, the tube mixed well by inversion and allowed to stand for 15 minutes at room temperature to allow the phage precipitate to form. The phage are pelleted by centrifugation at 12,000 in a tabletop microcentrifuge for 5 minutes, at 4° C. The supernate is removed and discarded. The pellet is resuspended in 100 µL T.E., then extracted with 50 µL phenol and nucleic acids are precipitated with ethanol and sodium acetate. Nucleic acids are resuspended in a final volume of 50 µL T.E.) Samples containing 1 µL of a 1:10–1:100 dilution of each unknown are then spotted on the filter membrane. The filter is baked at 80° C. in vacuo for 1 hour, prehybridized and hybridized to an appropriate singly biotinylated synthetic oligonucleotide probe, according to standard methods. The filter is washed briefly with 20× SSC at room temperature to remove unhybridized probe, blocked again with PBS containing 3% BSA for 30 minutes, and incubated with a solution containing 1 µm streptavidin-modified yellow-green fluorescent carboxylate-modified latex microspheres (0.2% solids final concentration). The filter membrane is then exposed to ultraviolet light at 300 nm and photographed using Polaroid black and white 667 print film, using a Kodak No. 15 or similar Wratten gelatin filter. The intensity of the spot containing the unknown sample is compared to the intensities of dilutions containing known amounts of M13 DNA, in order to determine the amount of DNA in the unknown sample.

EXAMPLE 18

Western Blot Detection

Spot blot detection of specific bovine heart cytochrome oxidase (COX) subunits using monoclonal antibodies and fluorescent microspheres. Bovine heart cytochrome c oxidase (COX), which contains 13 different subunits, is diluted into 0.02M Tris-Cl, 0.5M NaCl, 0.05% Tween 20, pH 7.5 (TTBS), and spotted directly onto nitrocellulose. Spots contain amounts such as 4 ng, 1 ng, 250 pg, 50 pg and 10 pg total protein. The membrane is then blocked with BLOTTO (Pierce), incubated with rabbit polyclonal antibodies directed against subunit IV. The membrane is washed with TTBS and then incubated with biotinylated goat anti-rabbit secondary antibodies, followed by a solution of PBS containing 0.28 µm yellow-green fluorescent streptavidin-coated carboxylate-modified latex microspheres (0.2% solids final concentration). Fluorescent spots are visualized using 254–360 nm excitation and photographed with Polaroid 667 black and white print film and a Kodak yellow Wratten filter. Subunit IV represents ~8.4% of the total protein. All spots show some detectable fluorescence, upon appropriate film exposures.

EXAMPLE 19

Detection of Antigens in Cells

Detection of nuclear antigens in human epithelial cells using human antinuclear (lupus) antibodies and fluorescent microspheres. Commercial preparations of human epithelial (Hep2) cells on microscope slides are obtained from Kallestad Diagnostics, Inc. Cells are blocked with PBS, 3% BSA, incubated with human antinuclear lupus antibodies diluted into PBS, washed with PBS, 0.2% Tween 20 and then incubated with biotinylated goat antihuman IgG (diluted in PBS). Slides are washed with PBS, 0.2% Tween 20, then incubated with 14 µm streptavidin-coated yellow-green fluorescent carboxylate-modifed microspheres and washed again to remove excess microspheres. Labeled nuclei are visualized using a standard fluorescein filter set and a fluorescence microscope.

EXAMPLE 20

Immunohistochemistry

Detection of antigens in retinal tissue using monoclonal antibodies and fluorescent microspheres. Zebrafish retinal tissue sections (16 μm, prepared according to standard procedures) are incubated for ½ hour in PBS containing 1% BSA and 0.5% Triton X-100, pH 7.2–7.4. The tissue is then probed with a monoclonal antibody directed against fish retinal antigens (FRet) (Larison and BreMiller, DEVELOPMENT 109, 567 (1990)), followed by sequential application of biotinylated goat anti-mouse, streptavidin and biotin-labeled 30 nm yellow-green fluorescent carboxylate-modified latex microspheres (all diluted in PBS containing 1% BSA and 0.05% Triton X-100, pH 7.2–7.4). Sections are washed in the same buffer to remove excess microspheres. Slides are cover-slipped and viewed through a standard fluorescein filter set using a fluorescence microscope. The nucleic acid stain, propidium iodide (0.5 μM) is added directly to the incubation and wash buffers, in order to label cell nuclei as a counterstain. This dye is visualized with standard rhodamine filters.

It is to be understood that, while the foregoing invention has been described in detail by way of illustration and example, only the preferred or specific embodiments have been revealed, and that numerous modifications, substitutions, and alterations are all permissible without departing from the spirit or scope of the invention as described in the following claims.

What is claimed is:

1. A method of applying a fluorescent label to a target specific binding pair member in a sample, comprising the steps of;
   a) combining the sample thought to contain the target specific binding pair member with a suspension of one or more microparticle-labeled probes, wherein each microparticle probe comprises
      a polymeric microparticle incorporating randomly dispersed therein a series of fluorescent dyes having an initial donor dye with a desired excitation peak and an ultimate acceptor dye with a desired emission peak, where each dye of the series has spectral overlap sufficient to allow for significant energy transfer of excitation energy to occur resulting in an effective Stokes shift; and
      a complementary specific binding pair member that binds to the target specific binding pair member and is covalently or non-covalently bound to the microparticle; and;
   b) allowing sufficient time for one or more microparticle-labeled probes to form a complex with the target specific binding pair member.

2. The method according to claim 1, wherein the series of fluorescent dyes in the microparticle comprises at least one polyazaindacene dye.

3. The method according to claim 2, wherein the series of fluorescent dyes comprises one to eight different polyazaindacene dyes.

4. The method according to claim 2, wherein the series of fluorescent dyes consists essentially of two to eight polyazaindacene dyes.

5. The method according to claim 2, wherein the polyazaindacene dyes have the formula:

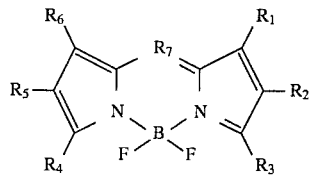

wherein $R_1$–$R_6$, which may be the same or different, are hydrogen, halogen, nitro, cyano, alkyl, perfluoroalkyl, alkoxy, alkenyl, alkynyl, cycloalkyl, arylalkyl, acyl (wherein the alkyl portions of each contain fewer than about 20 carbons); or substituted or unsubstituted aryl or heteroaryl; and $R_7$ is nitrogen; or methine; or halogen-, cyano-, alkyl-, perfluoroalkyl-, alkoxy-, alkenyl-, alkynyl-, cycloalkyl-, arylalkyl-, acyl-, (wherein the alkyl portions of each contain fewer than about 20 carbons) aryl- or heteroaryl-substituted methine; or $R_7$ is methine; or alkyl-, perfluoroalkyl-, cycloalkyl-substituted methine (wherein the alkyl portions of each contain fewer than about 20 carbons); or aryl- or heteroaryl-substituted methine; and adjacent substituents $R_1$–$R_2$, and $R_5$–$R_6$, each combine to form a fused benzo ring according to the formula (II):

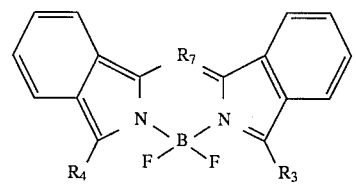

where each fused benzo ring optionally contains substituents, which may be the same or different, that are hydrogen, halogen, nitro, cyano, alkyl, perfluoroalkyl, alkoxy, alkenyl, alkynyl, cycloalkyl, alkylthio, alkylamido, amino, monoalkylamino, dialkylamino (wherein the alkyl portions of each contain fewer than about 20 carbons); or substituted or unsubstituted aryl, heteroaryl, aryl-amido, heteroaryl-amido, aryl-oxy, heteroaryl-oxy, aryl-amino, or heteroaryl-amino; or 1–2 additional fused benzo or heteroaromatic rings that are optionally unsubstituted or substituted.

6. The method according to claim 1, wherein the series of fluorescent dyes in the microparticle further comprises a hydrocarbon dye that is diphenylhexatriene, diphenylbutadiene, tetraphenylbutadiene, naphthalene, anthracene, pyrene, chrysene, rubrene, coronene, phenanthrene, or fluorene.

7. The method according to claim 1, wherein the complementary specific binding pair member is a biomolecule.

8. The method according to claim 7, wherein the target specific binding pair member is an amino acid, a peptide, or a protein.

9. The method according to claim 7, wherein the complementary specific binding pair member is a protein selected from the group consisting of avidin, strepavidin, and an antibody.

10. A method according to claim 7, wherein the target specific binding pair member is a nucleotide, oligonucleotide, or nucleic acid.

11. The method according to claim 10, wherein the nucleic acid is an RNA or a single-stranded or multi-stranded DNA.

12. The method according to claim 7, wherein the target specific binding pair member is a monosaccharide, polysaccharide, glycolipid, or glycoprotein.

13. The method according to claim 7, wherein the target specific binding pair member is a virus or bacteria.

14. The method according to claim 1, wherein the target specific binding pair member is a hapten.

15. The method according to claim 1, wherein the sample is a cell or cell extract.

16. The method according to claim 1, wherein the sample is absorbed on a solid or semi-solid support.

17. The method according to claim 1, further comprising the steps of illuminating the sample with means for exciting fluorescence in the microparticle-labeled probes; and detecting the fluorescence of the microparticle-labeled probes that have formed a complex with the target specific binding pair members.

18. The method according to claim 17, wherein the fluorescence is detected using means for magnification of the complex formed with the target specific binding pair members.

19. The method according to claim 17, wherein the fluorescence is detected using a flow cytometer.

20. A method of detecting multiple different target specific binding pair member in a sample using one fluorescent label, comprising the steps of;

a) preparing a sample thought to contain up to n different target specific binding pair members, where n is an integer greater than 1;

b) preparing a suspension of microparticle-labeled probes, wherein said microparticle-labeled probes comprise
polymeric microparticles incorporating randomly dispersed therein a series of fluorescent dyes having an initial donor dye with a desired excitation peak and an ultimate acceptor dye with a desired emission peak, where each dye in the series has spectral overlap sufficient to allow for significant energy transfer of excitation energy to occur resulting in an effective Stokes shift; and up to n complementary specific binding pair members that bind to the different target specific binding pair members, where each complementary specific binding pair member is covalently or non-covalently bound to the microparticle; such that the microparticle-labeled probes are capable of forming a complex with all target specific binding pair members in the sample;

c) combining the suspension with the sample to allow the microparticle-labeled probes to form a complex with the target specific binding pair members;

d) illuminating the sample with means for exciting fluorescence in the micro-particle-labeled probes; and e) detecting the fluorescence of the microparticle-labeled probes that have formed a complex with the target specific binding pair members.

21. A method according to claim 20, wherein the series of fluorescent dyes in the microparticle comprises at least one polyazaindacene dye of the formula:

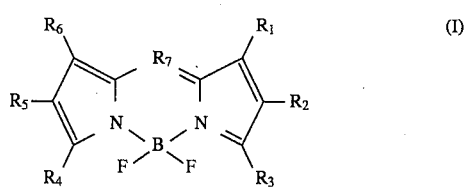

wherein $R_1$–$R_6$, which may be the same or different, are hydrogen, halogen, nitro, cyano, alkyl, perfluoroalkyl, alkoxy, alkenyl, alkynyl, cycloalkyl, arylalkyl, acyl (wherein the alkyl portions of each contain fewer than about 20 carbons); or substituted or unsubstituted aryl or heteroaryl; and $R_7$ is nitrogen; or methine; or halogen-, cyano-, alkyl-, perfluoroalkyl-, alkoxy-, alkenyl-, alkynyl-, cycloalkyl-, arylalkyl-, acyl-, (wherein the alkyl portions of each contain fewer than about 20 carbons) aryl- or heteroaryl-substituted methine; or $R_7$ is methine; or alkyl-, perfluoroalkyl-, cycloalkyl-substituted methine (wherein the alkyl portions of each contain fewer than about 20 carbons); or aryl- or heteroaryl-substituted methine; and adjacent substituents $R_1$–$R_2$, and $R_5$–$R_6$, each combine to form a fused benzo ring according to the formula (II):

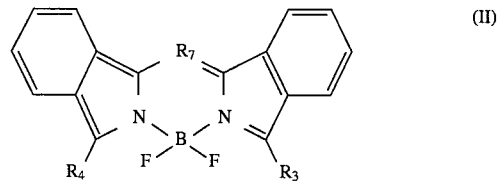

where each fused benzo ring optionally contains substituents, which may be the same or different, that are hydrogen, halogen, nitro, cyano, alkyl, perfluoroalkyl, alkoxy, alkenyl, alkynyl, cycloalkyl, alkylthio, alkylamido, amino, monoalkylamino, dialkylamino (wherein the alkyl portions of each contain fewer than about 20 carbons); or substituted or unsubstituted aryl, heteroaryl, aryl-amido, heteroaryl-amido, aryl-oxy, heteroaryl-oxy, aryl-amino, or heteroaryl-amino; or 1–2 additional fused benzo or heteroaromatic rings that are optionally unsubstituted or substituted.

22. The method according to claim 20, wherein the fluorescence is detected using means for magnification of the complex formed with the target specific binding pair members.

23. The method according to claim 20, wherein the fluorescence is detected using a flow cytometer.

24. A method of detecting multiple different target specific binding pair member in a sample using multiple fluorescent labels, comprising the steps of;

a) preparing a sample thought to contain up to n different target specific binding pair members, where n is an integer greater than 1;

b) preparing a suspensions of n different microparticle-labeled probes, wherein at least one microparticle-labeled probe comprises
a polymeric microparticle incorporating randomly dispersed therein a series of fluorescent dyes having an initial donor dye with a desired excitation peak and an ultimate acceptor dye with a desired emission peak, where each dye in the series has spectral overlap sufficient to allow for significant energy transfer of excitation energy to occur resulting in an effective Stokes shift; and a complementary specific binding pair member that binds to a corresponding target specific binding pair member, where the complementary specific binding pair member is covalently or non-covalently bound to the microparticle; where each different microparticle-labeled probe has detectably distinct spectral properties and forms a complex with a different corresponding target specific binding pair member;

c) combining the suspensions, collectively or sequentially, with the sample to allow each different microparticle-labeled probe to form a complex with a different corresponding target specific binding pair member;

d) illuminating the sample, simultaneously or sequentially, with means for exciting fluorescence in the microparticle-labeled probes; and e) detecting the fluorescence of the microparticle-labeled probes that have formed a complex with the target specific binding pair members.

25. The method according to claim 24, wherein the series of fluorescent dyes in the microparticle comprises at least one polyazaindacene dye of the formula:

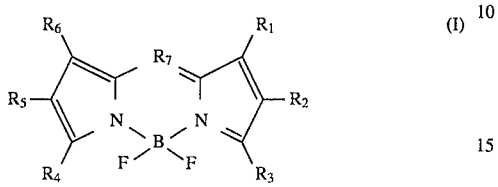

wherein $R_1$–$R_6$, which may be the same or different, are hydrogen, halogen, nitro, cyano, alkyl, perfluoroalkyl, alkoxy, alkenyl, alkynyl, cycloalkyl, arylalkyl, acyl (wherein the alkyl portions of each contain fewer than about 20 carbons); or substituted or unsubstituted aryl or heteroaryl; and $R_7$ is nitrogen; or methine; or halogen-, cyano-, alkyl-, perfluoroalkyl-, alkoxy-, alkenyl-, alkynyl-, cycloalkyl-, arylalkyl-, acyl- (wherein the alkyl portions of each contain fewer than about 20 carbons) aryl- or heteroaryl-substituted methine; or $R_7$ is methine; or alkyl-, perfluoroalkyl-, cycloalkyl-substituted methine (wherein the alkyl portions of each contain fewer than about 20 carbons); or aryl- or heteroaryl-substituted methine; and adjacent substituents $R_1$–$R_2$, and $R_5$–$R_6$, each combine to form a fused benzo ring according to the formula (II):

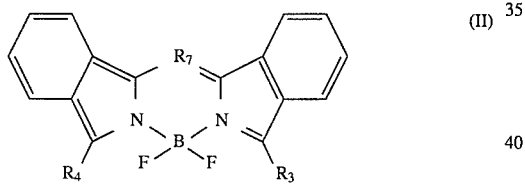

where each fused benzo ring optionally contains substituents, which may be the same or different, that are hydrogen, halogen, nitro, cyano, alkyl, perfluoroalkyl, alkoxy, alkenyl, alkynyl, cycloalkyl, alkylthio, alkylamido, amino, monoalkylamino, dialkylamino (wherein the alkyl portions of each contain fewer than about 20 carbons); or substituted or unsubstituted aryl, heteroaryl, aryl-amido, heteroaryl-amido, aryl-oxy, heteroaryl-oxy, aryl-amino, or heteroaryl-amino; or 1–2 additional fused benzo or heteroaromatic rings that are optionally unsubstituted or substituted.

26. The method according to claim 24, wherein the means for exciting fluorescence simultaneously excites fluorescence in a plurality of microparticle-labeled probes.

27. The method according to claim 24, wherein the polymeric microparticle of each different microparticle-labeled probe has a different maximal emission wavelength.

28. A method of detecting multiple different target specific binding pair members in a sample using mixtures of fluorescent labels, comprising the steps of;

a) preparing a sample thought to contain up to n different target specific binding pair members, where n is an integer greater than 2;

b) preparing n different mixtures of m different microparticle-labeled probes, where m is an integer greater than 1 and less than n, and where at least one microparticle-labeled probe comprises a polymeric microparticle incorporating randomly dispersed therein a series of fluorescent dyes having an initial donor dye with a desired excitation peak and an ultimate acceptor dye with a desired emission peak, where each dye in the series has spectral overlap sufficient to allow for significant energy transfer of excitation energy to occur resulting in an effective Stokes shift; and a complementary specific binding pair member that binds to a corresponding target specific binding pair member, where the complementary specific binding pair member is covalently or non-covalently bound to the microparticle; where each different microparticle-labeled probe has detectably distinct spectral properties and where each mixture has a characteristic percentage of each m microparticle-labeled probes that gives the mixture detectably distinct spectral properties, wherein the microparticle-labeled probes in any given mixture have the same complementary specific binding pair member;

c) combining the mixtures, collectively or sequentially, with the sample to allow each microparticle-labeled probe to form a complex with its corresponding target specific binding pair member;

d) illuminating the sample, simultaneously or sequentially, with means for exciting fluorescence in the microparticle-labeled probes; and e) detecting the fluorescence of the microparticle-labeled probes that have formed a complex with their target specific binding pair members.

29. The method, according to claim 28, where n/m is greater than 2.0.

30. The method according to claim 28, wherein the series of fluorescent dyes in the microparticle comprises at least one polyazaindacene dye of the formula:

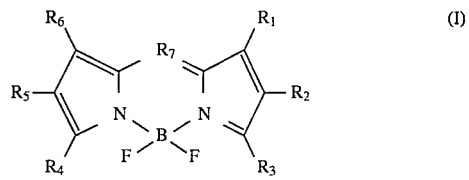

wherein $R_1$–$R_6$, which may be the same or different, are hydrogen, halogen, nitro, cyano, alkyl, perfluoroalkyl, alkoxy, alkenyl, alkynyl, cycloalkyl, arylalkyl, acyl (wherein the alkyl portions of each contain fewer than about 20 carbons); or substituted or unsubstituted aryl or heteroaryl; and $R_7$ is nitrogen; or methine; or halogen-, cyano-, alkyl-, perfluoroalkyl-, alkoxy-, alkenyl-, alkynyl-, cycloalkyl-, arylalkyl-, acyl- (wherein the alkyl portions of each contain fewer than about 20 carbons) aryl- or heteroaryl-substituted methine; or $R_7$ is methine; or alkyl-, perfluoroalkyl-, cycloalkyl-substituted methine (wherein the alkyl portions of each contain fewer than about 20 carbons); or aryl- or heteroaryl-substituted methine; and adjacent substituents $R_1$–$R_2$, and $R_5$–$R_6$, each combine to form a fused benzo ring according to the formula (II):

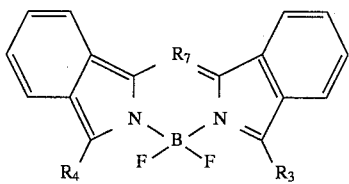 (II)

where each fused benzo ring optionally contains substituents, which may be the same or different, that are hydrogen, halogen, nitro, cyano, alkyl, perfluoroalkyl, alkoxy, alkenyl, alkynyl, cycloalkyl, alkylthio, alkylamido, amino, monoalkylamino, dialkylamino (wherein the alkyl portions of each contain fewer than about 20 carbons); or substituted or unsubstituted aryl, heteroaryl, aryl-amido, heteroaryl-amido, aryl-oxy, heteroaryl-oxy, aryl-amino, or heteroaryl-amino; or 1–2 additional fused benzo or heteroaromatic rings that are optionally unsubstituted or substituted.

* * * * *